(12) United States Patent
Kumar et al.

(10) Patent No.: US 7,297,678 B2
(45) Date of Patent: *Nov. 20, 2007

(54) USE OF REPEAT SEQUENCE PROTEIN POLYMERS IN PERSONAL CARE COMPOSITIONS

(75) Inventors: Manoj Kumar, Fremont, CA (US); William A. Cuevas, San Francisco, CA (US)

(73) Assignee: Genencor International, Inc., Palo Alto, CA (US)

( * ) Notice: Subject to any disclaimer, the term of this patent is extended or adjusted under 35 U.S.C. 154(b) by 123 days.

This patent is subject to a terminal disclaimer.

(21) Appl. No.: 10/800,179

(22) Filed: Mar. 12, 2004

(65) Prior Publication Data

US 2004/0180027 A1   Sep. 16, 2004

Related U.S. Application Data

(60) Provisional application No. 60/454,077, filed on Mar. 12, 2003.

(51) Int. Cl.
*A61K 38/00* (2006.01)
*C07K 2/00* (2006.01)

(52) U.S. Cl. .......................................... 514/2; 530/300
(58) Field of Classification Search ...................... 514/2
See application file for complete search history.

(56) References Cited

U.S. PATENT DOCUMENTS

| | | | | |
|---|---|---|---|---|
| 4,474,763 A * | 10/1984 | Lubowe | ........................ | 514/21 |
| 5,196,185 A * | 3/1993 | Silver et al. | ................... | 424/45 |
| 5,243,038 A | 9/1993 | Ferrari et al. | | |
| 5,412,074 A | 5/1995 | Jones et al. | | |
| 5,606,019 A * | 2/1997 | Cappello | .................... | 530/329 |
| 5,626,853 A | 5/1997 | Bara et al. | | |
| 5,627,148 A | 5/1997 | Dubief et al. | | |
| 5,672,336 A * | 9/1997 | Sharma | ........................ | 424/45 |
| 5,679,543 A | 10/1997 | Lawlis | | |
| 5,723,588 A * | 3/1998 | Donofrio et al. | ............ | 530/350 |
| 5,770,697 A * | 6/1998 | Ferrari et al. | ................ | 530/353 |
| 5,808,012 A * | 9/1998 | Donofrio et al. | ............ | 525/54.1 |
| 5,916,542 A * | 6/1999 | Fossati | .......................... | 424/59 |
| 5,945,086 A * | 8/1999 | Bassi et al. | ..................... | 424/45 |
| 6,004,444 A | 12/1999 | Aksay et al. | | |
| 6,017,534 A | 1/2000 | Malvar et al. | | |
| 6,018,030 A * | 1/2000 | Ferrari et al. | ................ | 530/353 |
| 6,033,654 A * | 3/2000 | Stedronsky et al. | ..... | 424/78.02 |
| 6,034,220 A | 3/2000 | Stedronsky | | |
| 6,140,072 A * | 10/2000 | Ferrari et al. | ............... | 435/69.1 |
| 6,153,602 A | 11/2000 | Dubief et al. | | |
| 6,184,348 B1 * | 2/2001 | Ferrari et al. | ................ | 530/350 |
| 6,228,248 B1 | 5/2001 | Aksay et al. | | |
| 6,355,776 B1 * | 3/2002 | Ferrari et al. | ................ | 530/350 |
| 6,358,501 B1 | 3/2002 | Dietz et al. | | |
| 6,365,661 B1 | 4/2002 | Fischer et al. | | |
| 6,365,877 B1 | 4/2002 | Chen et al. | | |
| 6,368,606 B1 | 4/2002 | Dubief et al. | | |
| 6,380,154 B1 * | 4/2002 | Cappello et al. | ................ | 514/2 |
| 6,423,333 B1 * | 7/2002 | Stedronsky et al. | ......... | 424/423 |
| 2001/0006664 A1 | 7/2001 | Ensley | | |
| 2001/0013294 A1 | 8/2001 | Bruno et al. | | |
| 2001/0027570 A1 | 10/2001 | Blees | | |
| 2002/0045567 A1 * | 4/2002 | Cappello et al. | ................ | 514/2 |
| 2002/0064539 A1 | 5/2002 | Philippe et al. | | |
| 2002/0147154 A1 * | 10/2002 | Wolfinbarger | ................ | 514/21 |
| 2003/0104589 A1 * | 6/2003 | Stedronsky et al. | ......... | 435/174 |
| 2003/0124152 A1 * | 7/2003 | Pang | .......................... | 424/401 |
| 2003/0176355 A1 * | 9/2003 | Cappello et al. | ............... | 514/17 |
| 2004/0014186 A1 * | 1/2004 | Kumar | ........................ | 435/168 |
| 2004/0180027 A1 * | 9/2004 | Kumar et al. | ............. | 424/70.14 |
| 2004/0228913 A1 * | 11/2004 | Kumar et al. | ................ | 424/468 |
| 2004/0234609 A1 * | 11/2004 | Collier et al. | ................ | 424/488 |
| 2005/0142094 A1 * | 6/2005 | Kumar | ..................... | 424/70.14 |

FOREIGN PATENT DOCUMENTS

| | | |
|---|---|---|
| EP | 0 540 357 A2 | 5/1993 |
| EP | 0 699 431 A1 | 3/1996 |
| WO | WO 9524478 A1 * | 9/1995 |
| WO | WO 00/35993 | 6/2000 |
| WO | WO 01/46213 A2 | 6/2001 |
| WO | WO 01/87825 A1 | 11/2001 |

OTHER PUBLICATIONS

D. Voet and J.G. Voet. Collagen in: Biochemistry. (1995) pp. 156-161.*
J. Crissman, et al. J. Control. Rel. (1998) 53, pp. 105-117.*
Deming, Facile synthesis of block copolypeptides of defined architecture, Nature, vol. 390, Nov. 27, 1997, pp. 386-389.
Fan et al., Rapid prototyping of patterned functional nanostructures, Nature, vol. 405, May 4, 2000, pp. 56-60.
Brott et al., Ultrafast holographic nanopatterning of biocatalytically formed silica, Nature, vol. 413, Sep. 20, 2001, pp. 291-293.
Huo et al., Generalized synthesis of periodic surfactant/Inorganic composite materials, Nature, vol. 368, Mar. 24, 1994, pp. 317-321.
Zhou et al., Efficient Catalysis of Polysiloxane Synthesis by Silicateinα Requires Specific Hydroxy and Imidazole Functionalities, Agnew. Chem. Inst., Ed. 1999, 38, No. 6, pp. 779-782.
Gosline et al., Elastic proteins: biological roles and mechanical properties, The Royal Society, Feb. 28, 2002, pp. 121-132.
Kroger et al., Polycationic Peptides from Diatom Biosilica That Direct Silica Nanosphere Formation, Science, vol. 286, Nov. 5, 1999, pp. 1129-1132.

(Continued)

*Primary Examiner*—Cecilia J. Tsang
*Assistant Examiner*—Andrew D Kosar
(74) *Attorney, Agent, or Firm*—Dinsmore & Shohl LLP

(57) ABSTRACT

A personal care composition is provided and includes an effective amount of a repeat sequence protein polymer. The personal care composition may be a hair care composition, a skin care composition, a nail care composition, a cosmetic composition, or an over-the-counter pharmaceutical composition.

21 Claims, 3 Drawing Sheets

OTHER PUBLICATIONS

Naik et al., Silica-Precipitating Peptides Isolated from a Combinatorial Phage Display Peptide Library, Journal of Nanoscience and Nanotechnology, 2002, vol. 2, No. 1, pp. 95-100.

Kroger et al., Silica-precipitating Peptides from Diatoms, The Chemical Structure of Silaffin-1A From Cylindrotheca Fusiformis, J. Biol. Chem., vol. 276, Issue 28, 26066-26070, Jul. 13, 2001, pp. 1-12.

Mizutani et al., Silicic Acid Polymerization Catalyzed by Amines and Polyamines, Bull. Chem. Soc. Jpn., 71, 2017-2022 (1998).

Hatrgerink et al., Peptide-amphiphile nanofibers: A versatile scaffold for the preparation of self-assembling materials, PNAS, Apr. 16, 2002, vol. 99, No. 8, pp. 5133-5138.

Zhang, Emerging biological materials through molecular self-assembly, Elsevier, Biotechnology Advances 20 (2002) pp. 321-339.

Wong et al., Assembly of Nanoparticles into Hollow Spheres Using Block Copolypeptides, Nano Letters, vol. 0, No. 0, pp. A-E.

Arkles, Commercial Applications of Sol-Gel Derived Hybrid Materials, Mrs. Bulletin, May 2001, pp. 402-408.

Sarikaya, Biomimetics: Materials fabrication through biology, PNAS, Dec. 7, 1999, vol. 96, No. 25, pp. 14183-14185.

Alvarez, Engineering Protein Molecules for the Ordered Structuring of Silica, National Nanofabrication Users Network, pp. 82-83.

Coradin et al., Biogenic Silica Patterning: Simple Chemistry or Subtle Biology? ChemBioChem 2003, 3, pp. 1-9.

* cited by examiner

USE OF REPEAT SEQUENCE PROTEIN POLYMERS IN PERSONAL CARE COMPOSITIONS

RELATED APPLICATION

This application claims priority under 35 U.S.C. §119 of U.S. Provisional Application Ser. No. 60/454,077 filed Mar. 12, 2003.

STATEMENT OF JOINT RESEARCH AGREEMENT

The present invention, as defined by the claims herein, was made by parties to a Joint Research Agreement ("agreement") between Genencor International, Inc. and The Dow Corning Corporation.

FIELD OF THE INVENTION

The present invention relates to personal care compositions, and more particularly, to personal care compositions comprising an effective amount of a repeat sequence protein polymer.

BACKGROUND OF THE INVENTION

Proteins have been widely used as ingredients in personal care products to perform a variety of functions and to impart desired characteristics to product formulations. For example, proteins have been used to impart manageability and strength to hair, to moisturize skin and hair, and to provide film formation to improve the appearance of skin and hair. Proteins have also been used to provide durability properties to many personal care products.

However, such proteins may not exhibit all desired characteristics when used in personal care products. For example, natural silk proteins may impart durability but may also form tight, hard fibers that are not suitable for film formation. Also, many natural proteins have a low isoelectric point, which reduces the affinity of the protein for the negatively charged skin and hair. Additionally, when more than one protein is needed to impart all desired characteristics to a given formulation, the necessity of using more than one protein may increase the cost and production time for a given personal care product.

Furthermore, proteins generally have poor solubility due to high molecular weight and hydrophobicity. Commercially available proteins, including structural proteins such as silk and collagen, are typically chemically degraded giving a diverse mixture of molecular weight fragments with variable properties. As such, these proteins are often modified chemically to enhance solubility for inclusion in personal care products. However, even chemically modified proteins may not have all desired characteristics.

Thus, there remains a need in the art for personal care compositions that have desired characteristics without chemical modification of the proteins. There also remains a need in the art for a method of delivering a protein into a personal care composition so as to effectively deliver the protein in a useable form.

SUMMARY OF THE INVENTION

Accordingly, the present invention is directed to personal care compositions comprising an effective amount of a repeat sequence protein polymer. In one embodiment, the repeat sequence polymer comprises a repeating amino acid sequence unit derived from elastin, collagen, abductin, byssus, flagelliform silk, dragline silk, gluten high molecular weight subunit, titin, fibronectin, leminin, gliadin, glue polypolypeptide, ice nucleating protein, keratin mucin, RNA polymerase II, resalin or a mixture thereof.

In another embodiment of the of the invention, the repeat sequence protein polymer (RSPP) formula comprises:

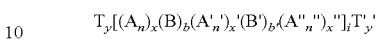

wherein: T and T' each comprise an amino acid or amino acid sequence of from about 1 to about 100 amino acids, wherein the amino acid or amino acid sequence of T' is the same as or different from the amino acid or amino acisequence of T; y and y' are each an integer from 0 to 1, wherein the integer of y' is the same as or different from the integer of y; A, A' and A" are each individual repeating amino acid sequence units comprising from about 3 to about 30 amino acids, wherein the amino acid sequence of A' and the amino acid sequence of A" are the same as or different from the amino acid sequence of A; n, n', and n" are each integers of at least 2 and not more than 250; x, x' and x" are each 0 or an integer of at least 1, wherein each integer varies to provide for at least 30 amino acids in the A', A' and A" individual amino acid sequence repeating units, and wherein the integer of x' and the integer of x" are the same as or different from the integer of x; B and B' each comprise an amino acid sequence of from about 4 to about 50 amino acids, wherein the amino sequence of B' is the same as or different from the amino acid sequence of B; b and b' are each an integer from 0 to 3, wherein the integer of b' is the same as or different from the integer of b; and i is an integer from 1 to 100.

In accordance with another embodiment of the present invention, the personal care composition comprises a hair care composition, a skin care composition, a nail care composition, a cosmetic composition, an over-the-counter pharmaceutical composition, or a combination thereof.

The personal care compositions comprising an effective amount of a repeat sequence protein polymer are advantageous in providing personal care products that have desired characteristic(s) without chemical modifications of the protein. These characteristics include but are not limited to, transparent film formation, hydrogel formation, better efficacy and binding to skin, hair, nail and oral surfaces, desired level of hydrophobicity with water solubility, imparting luster, softness, moisture retainment, mechanical properties (such as tensile properties, viscoelastic behavior, glass transition temperature, cloud temperature, and decomposition temperature). Still other advantages of the present invention will become apparent to those skilled in the art from the following detailed description where alternative exemplary embodiments of this invention are shown and described. As will be realized, the invention is capable of other different, obvious aspects and embodiments, all without departing from the invention. Accordingly, the drawings and descriptions should be regarded as illustrative in nature and not as restrictive.

DETAILED DESCRIPTION OF THE FIGURES

DETAILED DESCRIPTION OF THE PREFERRED EMBODIMENTS

Figure 1:
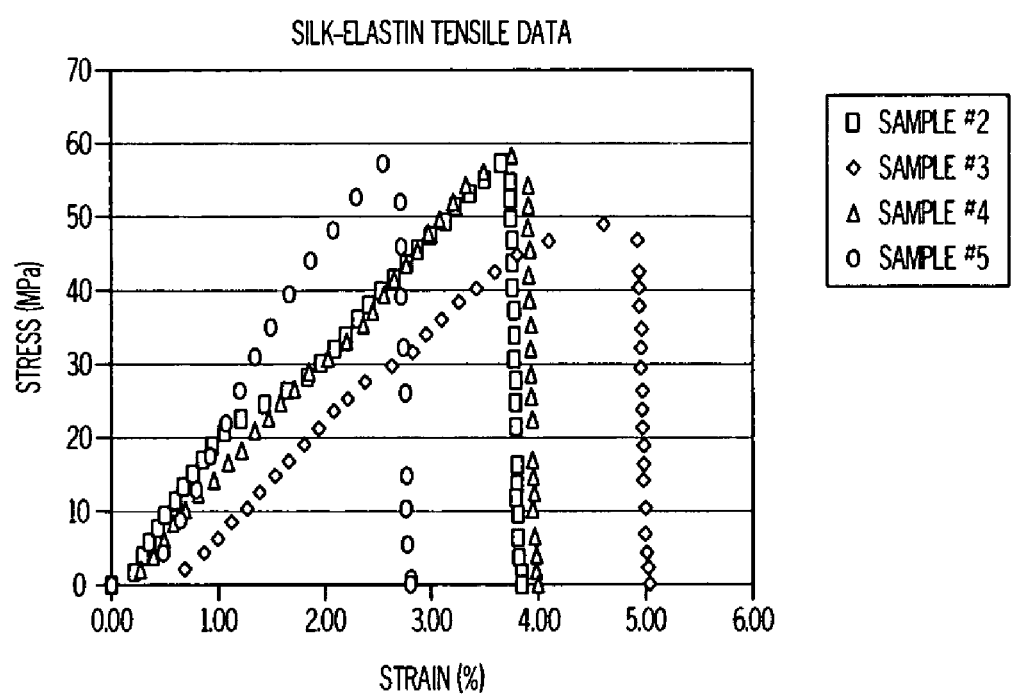
FIG. 1 is a chart illustrating stress strain curves of a repeat protein polymer in accordance with an embodiment of the present invention.

The present invention is directed to personal care compositions comprising an effective amount of a repeat sequence protein polymer. For purposes of defining and describing the present invention, "repeat sequence protein polymer" (RSPP) refers to a polymer comprising repeating amino acid sequence units, which repeating units are derived from a natural or synthetic protein. For example, the repeating sequence units may be derived from natural structure supporting materials such as silk, elastin, and collagen. Alternatively, the repeating sequence units may be derived from synthetic structures.

For purposes of defining and describing the present invention, "personal care composition" refers to a product for application to the skin, hair, nails, oral cavity and related membranes for the purposes of improving, cleaning, beautifying, therapeutically treating, caring for these surfaces and membranes.

For purposes of defining and describing the present invention, "an effective amount" refers to the amount of repeat sequence protein polymer which is added to a personal care composition to provide the composition with a desired characteristic or characteristics.

For purposes of defining and describing the technology, the term "dispersed phase" is a term well-known to one skilled in the art of emulsion technology, which means that the phase exists as small particles or droplets that are suspended in and surrounded by a continuous phase. The dispersed phase is also known as the internal or discontinuous phase.

One skilled in the art will appreciate the various naturally occurring proteins containing repeating sequence units which can be used for producing the repeat sequence protein polymers of the present invention, any of which may be employed herein. Specifically, there are more than six hundred repeating amino acid sequence units known to exist in biological systems. For example, well known proteins containing repeating amino acid sequence units include abductin, elastin, byssus, flagelliform silk, dragline silk, gluten high molecular weight (HMW) subunit, titin, fibronectin, leminin, and collagen.

Individual repeating amino acid sequence units of particular interest include units found in silk-, elastin-, collagen-, abductin-, byssus-, gluten-, titin-, extensin-, and fibronectin-like proteins. Silk-like proteins comprise a repeating sequence unit SGAGAG (SEQ ID NO. 1). This repeating sequence unit is found in naturally occurring silk fibroin protein, which can be represented as GAGAG (SGAGAG)$_8$SGAAGY (SEQ ID NO. 2). Elastin-like proteins comprise a base repeating sequence unit of GVGVP (SEQ ID NO. 3). This repeating sequence unit may be found in naturally occurring elastin. Collagen-like proteins comprise a repeating sequence unit of G-X-X$^1$, wherein X comprises any amino acid, often alanine or proline; and X$^1$ comprises any amino acid, often proline or hydroxy-proline (SEQ ID NO. 20). In one embodiment, collagen-like protein comprises SEQ ID NO. 29. Abductin-like proteins comprise a base repeating sequence unit of GGFGGMGGGX, wherein X comprises any amino acid (SEQ ID NO. 4). Byssus-like proteins comprise a repeating sequence unit of GPGGG (SEQ ID NO. 5). Gluten-like proteins of the high molecular weight subunit comprise repeating sequence units of PGQGQQ (SEQ ID NO. 6), GYYPTSPQQ (SEQ ID NO. 7), and GQQ (SEQ ID NO. 8). Titin-like proteins comprise repeating sequence units of PPAKVPEVPKKPVPEEKVPVPVPKK-PEA (SEQ ID NO. 9), which proteins may be found in the heart, psoas, and soleus muscle. Extensin-like proteins comprise repeating sequence units of SPPPPSPKYVYK (SEQ ID NO. 10). Fibronectin-like proteins comprise repeating sequence units of RGDS (SEQ ID NO. 11). Additional repeating sequence units are found, for example, in gliadin, glue polypolypeptide, ice nucleating protein, keratin, mucin, RNA polymerase II, and resilin. Gliadin comprises a repeating sequence unit of PQQPY (SEQ ID NO. 12). The glue polypeptide comprises a repeating sequence unit of PTTTK (SEQ ID NO. 13). The ice nucleating protein comprises a repeating sequence unit of AGYGSTGT (SEQ ID NO. 14). Keratin comprises repeating sequence units of YGGSSGGG (SEQ ID NO. 15) or FGGGS (SEQ ID NO. 16). Mucin comprises a repeating sequence unit of TTTPDV (SEQ ID NO. 17). RNA polymerase II comprises a repeating sequence unit of YSPTSPS (SEQ ID NO. 18).

In addition to repeating units derived from naturally occurring proteins, synthetic repeating amino acid sequences units may be utilized. In a particular embodiment, the repeat sequence protein polymer has the formula:

$$T_y[(A_n)_x(B)_b(A'_{n'})_x(B'')_{b'}(A''_{n''})_{x''}]_i T''_{y'}$$

wherein:

T and T' each comprise an amino acid or amino acid sequence of from about 1 to about 100 amino acids, specifically an amino acid or amino acid sequence of from about 1 to about 60 amino acids, and more specifically an amino acid or amino acid sequence with fewer than 20% of the total number of amino acids in the repeat sequence protein polymer, wherein the amino acid or amino acid sequence of T' is the same as or different from the amino acid sequence of T;

y and y' are each an integer from 0 to 1, wherein the integer of y' is the same as or different from the integer of y;

A, A' and A'' are each individual repeating sequence units comprising from about 3 to about 30 amino acids, wherein the amino acid sequence of A' and the amino acid sequence of A'' are the same as or different from the amino acid sequence of A;

n, n', and n'' are each integers of at least 2 and not more than 250;

x, x' and x'' are each 0 or an integer of at least 1, wherein each integer varies to provide for at least 30 amino acids in the A', A' and A'' individual repeating sequence units, and wherein the integer of x' and the integer of x'' are the same as or different from the integer of x;

B and B' each comprise an amino acid sequence of from about 4 to about 50 amino acids, wherein the amino sequence of B' is the same as or different from the amino acid sequence of B;

b and b' are each an integer from 0 to 3, wherein the integer of b' is the same as or different from the integer of b; and i is an integer from 1 to 100, specifically from 1 to 50, and more specifically from 1 to 30.

Additionally, the repeat sequence protein polymer may comprise amino acid sequences that link the repeating A, A', and A'' units or amino acid sequences that link between the individual A, A' or A'' repeating sequence units. In a particular embodiment, the linking sequences are from about 1 to about 10 amino acids.

One skilled in the art will appreciate the various methods for producing the repeat sequence protein polymers of the present invention, any of which may be employed herein. For example, the repeat sequence protein polymer may be produced by generally recognized methods of chemical synthesis, for example, L Andersson et. al., *Large-scale synthesis of peptides*, Biopolymers 55(3), 227-50 (2000)); genetic manipulation (for example, J. Cappello, Genetically Engineered Protein Polymers, Handbook of Biodegradable Polymers, Domb, A. J.; Kost, J.; Wiseman, D. (Eds.), Harvard Academic Publishers, Amsterdam; pages 387-414); and enzymatic synthesis (for example, C. H. Wong & K. T. Wang, *New Developments in Enzymatic Peptide Synthesis*, Experientia 47(11-12), 1123-9 (1991)). For example, the repeat sequence protein polymers of the present invention may be produced using the methods described in U.S. Pat. Nos. 5,243,038 and 6,355,776, the disclosures of which are incorporated by reference herein. In another example, the repeat sequence protein polymers may be produced utilizing non-ribosomal peptide synthase (for example, H. V. Dohren, et al., Multifunctional Peptide Synthase, Chem.Rev. 97, 2675-2705(1997). The repeat sequence protein polymers may also be produced on a commercial scale.

In producing the repeat sequence protein polymer, the repeating amino acid sequence units may comprise identical repeating sequence units or may comprise different repeating sequence unit combinations, which join together to form a block copolymer or an alternating block copolymer. Additionally, in one embodiment, the individual repeating amino acid sequence units of the repeat sequence protein polymer comprise from about 3 to about 30 amino acids. In another embodiment, the individual repeating units comprise from about 3 to about 8 amino acids. Moreover, the same amino acid may appear at least twice in the same repeating sequence unit.

Repeat sequence protein polymers utilizing natural and/or synthetic repeating sequence units may be produced to provide various desirable characteristics. One skilled in the art will appreciate the various desirable characteristics for repeat sequence protein polymers, any of which may be employed herein. The characteristics may include, for example, moisturizing properties, adhesion, contraction, entrapment, high glass transition temperature for hardness or strength, and/or to have a high cloud temperature for heat sensitive applications, or a high isoelectric point to increase the affinity of the protein to hair, skin, and nails. Self-assembly and nanofilament formation properties may be used for skin anti-wrinkle and fineline filling applications. Additionally, the molecular weight of the protein may also be chosen in order to increase or decrease water solubility or other properties as desired.

Furthermore, repeat sequence protein polymers are advantageous in providing personal care products when modified with desired chemical agents. RSPP's provide amino, hydroxyl and/or carboxyl functional groups that can be covalently reacted, conjugated, composited or ionically bonded with various personal care chemical and formulating functional ingredients. These can include: UV absorbers such as octyl methoxycinnamate, benzophenone-3, titanium dioxide, and octyl salicylate; film-forming agents such as VP/Eicosene copolymer; cosmeceutical agents such as peptides and proteins, alpha hydroxy acids, and retinol and retinoic acid derivatives; antioxidants such as tocopherol and derivatives thereof and ascorbic acid and derivatives thereof; vitamins such as B, D, K and their derivatives; antiperspirant actives such as aluminum hydroxide and zirconium hydroxide; depilating agents such as thioglycolate salts; anti-acne agents such as salicylic acid and benzoyl peroxide; abrasives and exfoliants such as silicates, pumice, and polyethylene; and extracts of plant, fruit, vegetable or marine sources.

It will also be understood by those having skill in the art that the synthetic repeat sequence protein polymers of embodiments of the present invention may also be produced to have a combination of desirable characteristics. For example, a copolymer comprising silk repeating sequence units and elastin repeating sequence units may be synthesized to impart durability due to the silk repeating sequence units and to impart flexibility due to the elastin repeating sequence units. Additionally, the silk-elastin polymer may exhibit other desirable properties such as good clear film and hydrogel formation, which the individual monomeric units may not exhibit. The silk elastin copolymer may be hydrophilic and water soluble. The silk elastin copolymer may also exhibit a high cloud temperature which is desirable in heat sensitive applications. The silk elastin copolymer may also have a high isoelectric point which may make the copolymer more substantive to skin and hair. The silk elastin copolymer may further exhibit self assembly into fibers and films which may be desirable in some applications.

Such characteristics may be provided, for example, with the choice of repeating amino acid sequence units, the number of repeating sequence units in each multimer, the spacing between the repeating sequence units, and the number of repeats of the multimer. For purposes of defining and describing the present invention, multimer refers to a portion of the repeat sequence protein polymer. Specifically, multimer refers to a portion of the repeat sequence protein polymer represented by $[(A_n)_x(B)_b(A'_{n'})_x'(B')_b(A''_{n''})_x'']_j$ in the above formula. The spacing between repeating sequence units refers to the other amino acid sequences represented by B or B' in the above formula. In one embodiment, the copolymers are combinations of silk units and elastin units to provide silk-elastin copolymers having properties distinctive from polymers having only the same monomeric unit.

It will be further understood by those having skill in the art that the repeat sequence protein polymers of the present invention may be monodispersed or polydispersed. For purposes of defining and describing the present invention, "monodispersed" polymers are polymers having a single defined molecular weight. For purposes of defining and describing the present invention, "polydispersed" polymers are polymers that have been subjected to proteolysis or other means of subdivision, and have a distribution of molecular weights.

In accordance with an embodiment of the present invention, a silk-elastin polymer SELP47K (SEQ ID NO. 19) may be used as the repeat sequence protein polymer of the present invention. The SELP47K is a homoblock protein polymer that consists exclusively of silk-like crystalline blocks and elastin-like flexible blocks. SELP47K is more linear than many proteins because it has a beta sheet two-dimensional structure rather than an alpha helix three-dimensional structure. SELP47K exhibits the ability to self-assemble by cross-linking of beta sheets into fibers. SELP47K is 70% proline, valine, and alanine, and has hydrophobic characteristics. Additionally, SELP47K has a high lysine ratio. In another embodiment, the repeat sequence protein polymer may comprise SELP 47-E13 (SEQ ID NO. 25), SELP 47R-3 (SEQ ID NO. 26), SELP 47K-3 (SEQ ID NO. 27), SELP 47 E-3 (SEQ ID NO. 28), SELP 67K (SEQ ID NO. 30), and SELP 58 (SEQ ID NO. 31).

Once a suitable repeat sequence protein polymer has been synthesized and purified, an effective amount may be added to a personal care composition. Personal care products can be classified/described as cosmetic, over-the-counter ("OTC") pharmaceutical, or therapeutic. For example, the repeat sequence protein polymer may be added to a personal care composition such as a hair care composition, a skin care composition, a nail care composition, a cosmetic composition, an over-the-counter pharmaceutical composition or a combination thereof.

In one embodiment, the hair care composition is in a form selected from the group consisting of shampoo, conditioner, anti-dandruff treatments, styling aids, styling conditioner, hair repair or treatment serum, lotion, cream, pomade, and chemical treatments. In another embodiment, the styling aids are selected from the group consisting of spray, mousse, rinse, gel, foam and a combination thereof. In another embodiment, the chemical treatments are selected from the group consisting of permanent waves, relaxers, and permanent, semi-permanent, and temporary color treatments and combinations thereof. In another embodiment, the skin care composition is in a form selected from the group consisting of moisturizing body wash, body wash, antimicrobial cleanser, skin protectant treatment, body lotion, facial cream, moisturizing cream, facial cleansing emulsion, surfactant-based facial cleanser, facial exfoliating gel, facial toner, exfoliating cream, facial mask, after shave balm and sunscreen.

In another embodiment, the cosmetic composition is in a form selected from the group consisting of eye gel, high-melting point lipstick, lipstick, lip gloss, lip balm, mascara, eyeliner, pressed powder formulation and foundation. In a further embodiment, the cosmetic composition comprises a makeup composition. Makeup compositions include, but are not limited to color cosmetics, such as mascara, lipstick, lip liner, eye shadow, eye liner, rouge, face powder, make up foundation, and nail polish. In yet another embodiment, the nail care composition is in a form selected from the group consisting of nail enamel, cuticle treatment, nail polish, nail treatment, and polish remover. In yet another embodiment, the oral care composition is in a form selected from the group consisting of toothpaste, mouth rinse, breath freshener, whitening treatment, and inert carrier substrates. In yet another embodiment, the over-the-counter pharmaceutical composition comprises sunscreen, anti-acne, antiperspirants, skin protectants, anti-dandruff products, anti-fungal, hemorrhoidal and toothpaste.

Moreover, the personal care composition may be in the form of an emulsified vehicle, such as a nutrient cream or lotion, a stabilized gel or dispersioning system, such as skin softener, a nutrient emulsion, a nutrient cream, a massage cream, a treatment serum, a liposomal delivery system, a topical facial pack or mask, a surfactant-based cleansing system such as a shampoo or body wash, an aerosolized or sprayed dispersion or emulsion, a hair or skin conditioner, styling aid, or a pigmented product such as makeup in liquid, cream, solid, anhydrous or pencil form.

In a specific embodiment, the repeat sequence protein polymer SELP47K may be used in a personal care composition. Specifically, SELP47K may have application to hair care products because it may build body or volume, repair damage, or protect hair from chemical damage. SELP47K may also have application to skin care products to provide, for example, tightening or firming of the skin, moisturization, improved skin tone, oil absorption, or improvement in the appearance of fine lines and wrinkles. SELP47K may additionally provide eyelash flexibility, volume, length, and strength.

In one embodiment, the repeat sequence protein polymer comprises from about 0.001% to about 10% by weight of the personal care composition. In another embodiment, the repeat sequence protein polymer comprises from about 0.01% to about 5% by weight of the personal care composition. In yet another embodiment, the repeat sequence protein polymer comprises from about 0.01% to about 1% by weight of the personal care composition.

The personal care composition comprising an effective amount of a repeat sequence protein polymer, as set forth herein, may comprise additional components. For example, the personal care composition may comprise liposomes, which liposomes may comprise, at least, water and one or more ingredients capable of forming lipid bilayer vesicles that can hold one or more functional or active ingredient(s). Non-limiting examples of ingredients capable of forming lipid bilayer vesicles include: phospholipids, hydrogenated phosphatidylcholine, lecithin, cholesterol and sphingolipids. Non-limiting examples of functional or active ingredients that can be delivered from liposomes include: vitamins and their derivatives, antioxidants, proteins and peptides, keratolytic agents, bioflavinoids, terpenoids, phytochemicals, and extracts of plant, marine or fermented origin. In one embodiment, liposomes include, without limitation: a) lipoid liposome 0003 (composed of water and lecithin and glycerin); b) lipoid liposome 0300 (composed of water and phosphatidylcholine), c) lipoid liposome 0111 (composed of water, ginkgo balboa leaf extract, denatured alcohol, hydrogenated lecithin and cholesterol) d) anti-irritant liposomes (composed of water, cola acuminata seed extract, bisabolol and phospholipids), e) vitamin C and E liposomes (composed of water, phospholipids, tocopheryl acetate and ascorbyl palmitate), f) firming liposomes (composed of water, butylene glycol, pyrus malus (Apple) fruit extract, phospholipids, tocopheryl acetate and carbomer) and g) moisturizing liposomes (composed of water, sodium PCA, tocopheryl acetate, xanthan gum, arginine, lysine, glycine and proline).

In another embodiment, the personal care composition may further comprise an active ingredient. One skilled in the art will appreciate the various active ingredients for use in personal care compositions, any of which may be employed herein, see e.g., McCutcheon's *Functional Materials*, North American and International Editions, (2003), published by MC Publishing Co. For example, the personal care compositions herein may comprise a skin care active ingredient at a level from about 0.0001% to about 20%, by weight of the composition. In another embodiment, the personal care composition comprises a skin care active ingredient from about 0.001% to about 5%, by weight of the composition. In yet another embodiment, the personal care composition comprises a skin care active ingredient from about 0.01% to about 2%, by weight of the composition.

Skin care active ingredients include, but are not limited to, antioxidants, such as tocopheryl and ascorbyl derivatives; bioflavinoids, terpenoids, synthetics of biolflavinoids and terpenoids and the like; vitamins and vitamin derivatives; hydroxyl- and polyhydroxy acids and their derivatives, such as AHAs and BHAs and their reaction products; peptides and polypeptides and their derivatives, such as glycopeptides and lipophilized peptides, heat shock proteins and cytokines; enzymes and enzymes inhibitors and their derivatives, such as proteases, MMP inhibitors, catalases, CoEnzyme Q10, glucose oxidase and superoxide dismutase (SOD); amino acids and their derivatives; bacterial, fungal and yeast fermentation products and their derivatives, including mushrooms, algae and seaweed and their derivatives; phytosterols and plant and plant part extracts; phospholipids and their derivatives; anti-dandruff agents, such as zinc pyrithione, and sunscreen agents such as ethylhexyl methoxycinnamate, avobenzone, and phenyl benzimidazole sulfonic acid. Delivery systems comprising the active ingredients are also provided herein.

In one embodiment, the skin care active ingredient is selected from the group consisting of a Vitamin B3 component, panthenol, Vitamin E, Vitamin E acetate, retinoid, retinol, retinyl, propionate, retinyl palmitate, retinoic acid, Vitamin C, theobromine, alpha-hydroxyacid, farnesol, phytrantriol, salicylic acid, palmityl peptapeptide-3 and mixtures thereof. In another embodiment, the Vitamin B3 compound is niacinamide. In yet another embodiment, the vitamin $B_3$ compound is tocopherol nicotinate.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide. Suitable esters of nicotinic acid include nicotinic acid esters of $C_1$-$C_{22}$, specifically $C_1$-$C_{16}$, more specifically $C_1$-$C_6$ alcohols. The alcohols are suitably straight-chain or branched chain, cyclic or acyclic, saturated or unsaturated (including aromatic), and substituted or unsubstituted. The esters are specifically non-vasodilating. Non-vasodilating esters of nicotinic acid include tocopherol nicotinate and inositol hexanicotinate. A more complete description of vitamin $B_3$ compounds is given in WO 98/22085.

The retinoid skin care active ingredient may be retinol, retinol esters (e.g., $C_2$-$C_{22}$ alkyl esters of retinol, including retinyl palmitate, retinyl acetate, retinyl proprionate), retinal, and/or retinoic acid (including all-trans retinoic acid and/or 13-cis-retinoic acid). These compounds are well known in the art and are commercially available from a number of sources, e.g., Sigma Chemical Company, and Boehringer Mannheim. Exemplary retinoids are retinol, retinyl palmitate, retinyl acetate, retinyl proprionate, retinal, retinoic propionate, retinoic acid and combinations thereof. The retinoid may be included as the substantially pure material, or as an extract obtained by suitable physical and/or chemical isolation from natural (e.g., plant) sources. The retinoid may comprise from about 0.005% to about 2% and speicifcally from about 0.01% to about 12% by weight of the personal care composition. In another embodiment, the personal care composition may comprise retinol. The retinol may comprise from about 0.01% to about 0.15% by weight of the personal care composition. In yet another embodiment, the personal care composition may comprise retinol esters. The retinol esters may comprise from about 0.01% to about 2% by weight of the personal care composition.

In addition to the active ingredients noted above, the personal care composition may comprise a physiologically acceptable carrier or excipient. Specifically, the personal care compositions herein may comprise a safe and effective amount of a dermatologically acceptable carrier, suitable for topical application to the skin or hair within which the essential materials and optional other materials are incorporated to enable the essential materials and optional components to be delivered to the skin or hair at an appropriate concentration. The carrier can thus act as a diluent, dispersant, solvent or the like for the essential components which ensures that they can be applied to and distributed evenly over the selected target at an appropriate concentration.

An effective amount of one or more compounds described herein may also be included in personal care compositions to be applied to keratinous materials such as nails and hair, including but not limited to those useful as hair spray compositions, hair styling compositions, hair shampooing and/or conditioning compositions, compositions applied for the purpose of hair growth regulation and compositions applied to the hair and scalp for the purpose of treating seborrhoea, dermatitis and/or dandruff.

An effective amount of one or more compounds described herein may be included in personal care compositions suitable for topical application to the skin, teeth, nails or hair. These compositions can be in the form of creams, lotions, gels, suspensions dispersions, microemulsions, nanodispersions, microspheres, hydrogels, emulsions (e.g., oil-in-water and water-in-oil, as well as multiple emulsions) and multilaminar gels and the like (see, for example, *The Chemistry and Manufacture of Cosmetics*, Schlossman et al., 1998), and may be formulated as aqueous or silicone compositions or may be formulated as emulsions of one or more oil phases in an aqueous continuous phase (or an aqueous phase in an oil phase).

The type of carrier utilized in the present invention depends on the type of product form desired for the personal care composition. The carrier can be solid, semi-solid or liquid. Suitable carriers are liquid or semi-solid, such as creams, lotions, gels, sticks, ointments, pastes, sprays and mousses. Specifically, the carrier is in the form of a lotion, cream or a gel, more specifically one which has a sufficient thickness or yield point to prevent the particles from sedimenting. The carrier can itself be inert or it can possess dermatological benefits of its own. The carrier may be applied directly to the teeth, skin, nails and/or hair or it may be applied via a woven or non-woven wipe or cloth. It may also be in the form of a patch, mask, wrap, or other inert substrate. It may also be aerosolized or otherwise sprayed or pumped onto the skin and/or hair. The carrier should also be physically and chemically compatible with the essential components described herein, and should not unduly impair stability, efficacy or other use benefits associated with the compositions of the present invention.

In one embodiment, the carrier may be selected from the group consisting of water, propylene glycol, ethanol, propanol, glycerol, butylene glycol and polyethylene glycol, or a combination thereof. The carriers may also contain a dermatologically acceptable, hydrophilic diluent. Suitable hydrophilic diluents include water, organic hydrophilic diluents such as $C_2$-$C_{10}$, specifically $C_2$-$C_6$, more specifically, $C_3$-$C_6$ monohydric alcohols and low molecular weight glycols and polyols, including propylene glycol, polyethylene glycol polypropylene glycol, glycerol, butylene glycol, 1,2,4-butanetriol, sorbitol, 1,2,6-hexametriol, pentylene glycol, hexylene glycol, sorbitol esters, ethoxylated ethers, propoxylated ethers and combinations thereof. In one embodiment, the diluent is a liquid. In another embodiment, the diluent is water. In another embodiment, the personal care composition comprises at least about 20% of the hydrophilic diluent.

Suitable carriers may also comprise an emulsion comprising a hydrophilic phase, especially an aqueous phase, and a hydrophobic phase e.g., a lipid, oil or oily material. As well known to one skilled in the art, the hydrophilic phase will be dispersed in the hydrophobic phase, or vice versa, to form respectively hydrophilic or hydrophobic dispersed and continuous phases, depending on the composition of ingredients. The emulsion may be or comprise (e.g., in a triple or other multi-phase emulsion) an oil-in-water emulsion or a water-in-oil emulsion such as a water-in-silicone emulsion.

Oil-in-water emulsions may comprise from about 1% to about 60% or from about 1% to about 30% of the dispersed hydrophobic phase and from about 1% to about 99% or from about 10% to about 90% of the continuous hydrophilic phase; water-in-oil emulsions may comprise from about 1% to about 98% or from about 40% to about 90% of the dispersed hydrophilic phase and from about 1% to about 50% or from about 1% to about 30% of the continuous hydrophobic phase.

The carrier might also include one or more components that facilitate penetration through the upper stratum corneum barrier to the deeper skin layers. Examples of penetration enhancers include, but are not limited to, propylene glycol, azone, ethoxydiglycol, dimethyl isosorbide, urea, ethanol and dimethyl sulfoxide. Other examples include, but are not limited to, microemulsions, liposomes and nanoemulsions.

The personal care compositions of the present invention may further comprise humectants. In one embodiment, the personal care composition comprises from about 0.01% to about 20% by weight of humectant. In another embodiment, the personal care composition comprises from about 0.1% to about 15% by weight of a humectant. In yet another embodiment, the personal care composition comprises from about 0.5% to about 10% by weight of a humectant. Humectants include, but are not limited to, compounds selected from polyhydric alcohols, sorbitol, glycerol, urea, betaine, D or DL panthenol, calcium pantothenate, royal jelly, panthetine, pantotheine, panthenyl ethyl ether, pangamic acid, pyridoxin, pantoyl lactose Vitamin B complex, sodium pyrrolidone carboxylic acid, hexane-1,2,6,-triol, guanidine or its derivatives, and mixtures thereof.

Suitable polyhydric alcohol humectants for use herein include polyalkylene glycols and specifically alkylene polyols and their derivatives, including propylene glycol, dipropylene glycol, polypropylene glycol, polyethylene glycol and derivatives thereof, sorbitol, hydroxypropyl sorbitol, erythritol, threitol, pentaerythritol, xylitol, glucitol, mannitol, pentylene glycol, hexylene glycol, butylene glycol (e.g., 1,3-butylene glycol), hexane triol (e.g., 1,2,6-hexanetriol), trimethylol propane, neopentyl glycol, glycerine, ethoxylated glycerine, propane-1,3 diol, propoxylated glycerine and mixtures thereof. The alkoxylated derivatives of any of the above polyhydric alcohols are also suitable for use herein. In one embodiment, polyhydric alcohols of the present invention are selected from glycerine, butylene glycol, propylene glycol, pentylene glycol, hexylene glycol, dipropylene glycol, polyethylene glycol, hexane triol, ethoxylated glycerine and propoxylated glycerine and mixtures thereof.

Suitable humectants useful herein are sodium 2-pyrrolidone-5-carboxylate (NaPCA), guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; betaine, panthenol and derivatives thereof; and mixtures thereof.

At least part (up to about 5% by weight of composition) of a humectant may be incorporated in the form of an admixture with a particulate cross-linked hydrophobic acrylate or methacrylate copolymer, itself specifically present in an amount of from about 0.1% to about 10%, which can be added either to the aqueous or disperse phase. This copolymer is particularly valuable for reducing shine and controlling oil while helping to provide effective moisturization benefits and is described in further detail by WO96/03964.

The oil-in-water and oil-in-water-in-oil emulsion embodiments of the present invention may comprise from about 0.05% to about 20%, specifically from about 1% to about 15%, more specifically from about 2% to about 10%, and even more specifically from about 2% to about 5% by weight of a dermatologically acceptable emollient. Emollients tend to lubricate the skin, increase the smoothness and suppleness of the skin, prevent or relieve dryness of the skin and/or protect the skin. Emollients are typically water-immiscible, oily or waxy materials and emollients with high molecular weights can confer aesthetic properties to a topical composition. A wide variety of suitable emollients are known and may be used herein. Sagarin, *Cosmetics, Science and Technology*, 2nd Edition, Vol. 1, pp. 32-43 (1972), contains numerous examples of materials suitable as an emollient. All emollients discussed in application WO 00/24372 should be considered as suitable for use in the present invention although examples are outlined in further detail below:

i) Straight and branched chain hydrocarbons having from about 7 to about 40 carbon atoms, such as mineral oils, dodecane, squalane, cholesterol, hydrogenated polyisobutylene, isohexadecane, isoeicosane, isooctahexacontane, isohexapentacontahectane, and the $C_7$-$C_{40}$ isoparaffins, which are $C_7$-$C_{40}$ branched hydrocarbons. Suitable branched chain hydrocarbons for use herein are selected from isopentacontaoctactane, petrolatum and mixtures thereof;

ii) $C_1$-$C_{30}$ fatty acid esters of $C_1$-$C_{30}$ carboxylic acids, $C_{12-15}$ 12-15 alkyl benzoates and of $C_2$-$C_{30}$ dicarboxylic acids, e.g. isononyl isononanoate, isostearyl neopentanoate, isodecyl octanoate, isodecyl isononanoate, tridecyl isononanoate, myristyl octanoate, octyl pelargonate, octyl isononanoate, myristyl myristate, myristyl neopentanoate, myristyl octanoate, isopropyl myristate, myristyl propionate, isopropyl stearate, isopropyl isostearate, methyl isostearate, behenyl behenate, dioctyl maleate, diisopropyl adipate, and diisopropyl dilinoleate and mixtures thereof;

iii) $C_1$-$C_{30}$ mono- and poly-esters of sugars and related materials derived from a sugar or polyol moiety and one or more carboxylic acid moieties. Depending on the constituent acid and sugar, these esters can be in either liquid or solid form at room temperature. Examples include: glucose tetraoleate, the galactose tetraesters of oleic acid, the sorbitol tetraoleate, sucrose tetraoleate, sucrose pentaoleate, sucrose hexaoleate, sucrose heptaoleate, sucrose octaoleate, sorbitol hexaester. Other materials include cottonseed oil or soybean oil fatty acid esters of sucrose. Other examples of such materials are described in WO 96/16636;

iv) Vegetable oils and hydrogenated vegetable oils. Examples of vegetable oils and hydrogenated vegetable oils include safflower oil, grapeseed oil, coconut oil, cottonseed oil, menhaden oil, palm kernel oil, palm oil, peanut oil, soybean oil, rapeseed oil, linseed oil, rice bran oil, pine oil, nut oil, sesame oil, sunflower seed oil, partially and fully hydrogenated oils from the foregoing sources and mixtures thereof; and v) Soluble or colloidally-soluble moisturizing agents. Examples include hyaluaronic acid and, chondroitin sulfate, heparan sulfate, and starch-grafted sodium polyacrylates.

Personal care compositions herein may also contain one or more emulsifiers and/or surfactants, generally to help disperse and suspend the disperse phase within the continuous phase. A surfactant may be useful if the product is intended for skin or hair cleansing. For convenience hereinafter emulsifiers will be referred to under the term "surfactants". Thus, surfactant(s) will be used to refer to surface active agents whether used as emulsifiers or for other surfactant purposes such as skin cleansing. Known or conventional surfactants can be used in the composition, provided that the selected agent is chemically and physically compatible with essential components of the composition and provides the desired characteristics. Suitable surfactants include non-silicone derived materials, silicone-derived materials, and mixtures thereof. All surfactants discussed in application WO 00/24372 should be considered as suitable for use in the present invention. The personal care compositions of the present invention may comprise from about 0.05% to about 30%, specifically from about 0.5% to 15%, and more specifically from about 1% to 10% by weight of a surfactant or mixture of surfactants. The exact surfactant or surfactant mixture chosen will depend upon the pH of the composition, the other components present and the desired final product aesthetics.

Among the nonionic surfactants that are useful herein are those that can be broadly defined as condensation products of long chain alcohols, e.g. $C_{8-30}$ alcohols, with sugar or starch polymers, i.e., glycosides. Other useful nonionic surfactants include the condensation products of alkylene oxides with fatty acids (i.e., alkylene oxide esters of fatty acids). These materials have the general formula $RCO(X)_n$OH wherein R is a $C_{10-30}$ alkyl group, X is —$OCH_2CH_2$— (i.e., derived from ethylene glycol or oxide) or —$OCH_2CHCH_3$— (i.e., derived from propylene glycol or oxide) and n is an integer from 6 to 200. Other nonionic surfactants are the condensation products of alkylene oxides with 2 moles of fatty acids (i.e., alkylene oxide diesters of fatty acids). These materials have the general formula $RCO(X)_nOOCR$ wherein R is a $C_{10-30}$ alkyl group, X is —$OCH_2CH_2$— (i.e., derived from ethylene glycol or oxide) or —$OCH_2CHCH_3$— (i.e., derived from propylene glycol or oxide) and n is an integer from 6 to 100. For example, an emulsifier for use herein is most specifically a fatty acid ester blend based on a mixture of sorbitan fatty acid ester and sucrose fatty acid ester, more specifically a blend of sorbitan stearate and sucrose cocoate. Even further suitable examples include a mixture of cetearyl alcohols and cetearyl glucosides.

The hydrophilic surfactants useful herein can alternatively or additionally include any of a wide variety of cationic, anionic, zwitterionic, and amphoteric surfactants such as are known in the art. (See, e.g., McCutcheon's, *Detergents and Emulsifiers and Detergents*, North American (2003) and International Editions (1986), published by MC Publishing Co. and Allured Publishing Corporation; U.S. Pat. No. 5,011,681 to Ciotti et al., U.S. Pat. No. 4,421,769 to Dixon et al.; and U.S. Pat. No. 3,755,560 to Dickert et al.).

A variety of anionic surfactants are also useful herein. (See, e.g., U.S. Pat. No. 3,929,678, to Laughlin et al.). Examples of anionic surfactants include the alkoyl isethionates (e.g., $C_{12}$-$C_{30}$), alkyl and alkyl ether sulfates and salts thereof, alkyl and alkyl ether phosphates and salts thereof, alkyl methyl taurates (e.g., $C_{12}$-$C_{30}$), and soaps (e.g., substituted alkylamine and alkali metal salts, e.g., sodium or potassium salts) of fatty acids.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (specifically $C_8$-$C_{18}$) and one contains an anionic water solubilizing group, e.g., carboxy, sulfonate, sulfate, phosphate, or phosphonate. Examples are alkyl imino acetates and iminodialkanoates and aminoalkanoates, imidazolinium and ammonium derivatives. Other suitable amphoteric and zwitterionic surfactants are those selected from the group consisting of betaines, sultaines, hydroxysultaines, and branched and unbranched alkanoyl sarcosinates, and mixtures thereof.

Some emulsions of the present invention may include a silicone containing emulsifier or surfactant. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains and polyether chains containing moieties derived from both ethylene oxide and propylene oxide. Other examples include alkyl-modified dimethicone copolyols, i.e., compounds which contain $C_2$-$C_{30}$ pendant side chains. Still other useful dimethicone copolyols include materials having various cationic, anionic, amphoteric, and zwitterionic pendant moieties.

The personal care compositions of the present invention may further comprise at least one polymeric thickening agent. The polymeric thickening agents useful herein may have a number average molecular weight of greater than about 20,000, specifically greater than about 50,000, and more specifically greater than about 100,000. The personal care compositions of the present invention may comprise from about 0.01% to about 10%, specifically from about 0.1% to about 8%, and more specifically from about 0.25% to about 5% by weight of a polymeric thickening agent or mixtures thereof.

Examples of polymer thickening agents for use herein include non-ionic thickening agents and anionic thickening agents or mixtures thereof. Suitable non-ionic thickening agents include polyacrylamide polymers, crosslinked poly (N-vinylpyrrolidones), polysaccharides, natural or synthetic gums, polyvinylpyrrolidone and polyvinylalcohol. Suitable anionic thickening agents include acrylic acid/ethyl acrylate copolymers, carboxyvinyl polymers and crosslinked copolymers of alkyl vinyl ethers and maleic anhydride. As an example, Noveon sells a thickener under the trademark of CARBOPOL™ resins or mixtures thereof. Suitable Carbopol resins may be hydrophobically modified, and other suitable resins are described in WO98/22085, or mixtures thereof.

The present personal care compositions may comprise at least one silicone oil phase. Silicone oil phase(s) generally comprises from about 0.1% to about 20%, specifically from about 0.5% to about 10%, and more specifically from about 0.5% to about 5% by weight of the composition. The silicone oil phase may comprise one or more silicone components.

Silicone components can be fluids, including straight chain, branched and cyclic silicones. Suitable silicone fluids useful herein include silicones inclusive of polyalkyl siloxane fluids, polyaryl siloxane fluids, cyclic and linear polyalkylsiloxanes, polyalkoxylated silicones, amino and quaternary ammonium modified silicones, polyalkylaryl siloxanes or a polyether siloxane copolymer and mixtures thereof. The silicone fluids can be volatile or non-volatile. Silicone fluids generally have an average molecular weight of less than about 200,000. Suitable silicone fluids have a molecular weight of about 100,000 or less, specifically about 50,000 or less, and more specifically about 10,000 or less. Particularly, the silicone fluid is selected from silicone fluids having a weight average molecular weight in the range from about 100 to about 50,000 and specifically from about 200 to about 40,000.

Typically, silicone fluids have a viscosity ranging from about 0.65 to about 600,000 $mm^2s^{-1}$, specifically from about 0.65 to about 10,000 $mm^2s^{-1}$ at 25° C. The viscosity can be measured by means of a glass capillary viscometer as set forth in Dow Corning Corporate Test Method CTM0004, Jul. 29, 1970. Suitable polydimethyl siloxanes that can be used herein include those available, for example, from the General Electric Company and from Dow Corning. Also useful are essentially non-volatile polyalkylarylsiloxanes, for example, polymethylphenylsiloxanes, having viscosities of about 0.65 to 30,000 $mm^2s^{-1}$ at 25° C. These siloxanes are available, for example, from the General Electric Company or from Dow Corning. Cyclic polydimethylsiloxanes suitable for use herein are those having a ring structure incorporating from about 3 to about 7 $(CH_3)_2SiO$ moieties, specifically about 5 or more.

Silicone gums may also be used herein. In specific embodiments, a silicone oil phase comprises a silicone gum or a mixture of silicones including the silicone gum. Typically, silicone gums have a viscosity at 25° C. in excess of about 1,000,000 $mm^2s^{-1}$. The silicone gums include dimethicones as described by Petrarch and others including U.S. Pat. No. 4,152,416, May 1, 1979 to Spitzer, et al, and Noll, Walter, *Chemistry and Technology of Silicones*, New York: Academic Press 1968. Also describing silicone gums are General Electric Silicone Rubber Product Data Sheets SE 30, SE 33, SE 54 and SE 76. Specific examples of silicone gums include polydimethylsiloxane, (polydimethylsiloxane) (methylvinylsiloxane) copolymer, poly(dimethylsiloxane) (diphenyl)(methylvinylsiloxane) copolymer and mixtures thereof. Preferred silicone gums for use herein are silicone gums having a molecular weight of from about 200,000 to about 4,000,000 selected from dimethiconol, dimethicone copolyol, dimethicone and mixtures thereof.

A silicone phase herein may comprise a silicone gum incorporated into the composition as part of a silicone gum-fluid blend. When the silicone gum is incorporated as part of a silicone gum-fluid blend, the silicone gum may constitute from about 5% to about 40% and specifically from about 10% to 20% by weight of the silicone gum-fluid blend. Suitable silicone gum-fluid blends herein are mixtures consisting essentially of:
  (i) a silicone having a molecular weight of from about 200,000 to about 4,000,000 selected from dimethiconol, fluorosilicone and dimethicone and mixtures thereof; and
  (ii) a carrier which is a silicone fluid, the carrier having a viscosity from about 0.65 $mm^2s^{-1}$ to about 100 $mm^2s^{-1}$, wherein the ratio of i) to ii) is from about 10:90 to about 20:80 and wherein said silicone gum-based component has a final viscosity of from about 100 $mm^2s^{-1}$ to about 100,000 $mm^2s^{-1}$, specifically from 500 $mm2s^{-1}$ to about 10,000 $mm^2s^{-1}$.

Further silicone components suitable for use in a silicone oil phase herein are crosslinked polyorganosiloxane polymers, optionally dispersed in a fluid carrier. In general, when present the crosslinked polyorganosiloxane polymers, together with their carrier (if present) comprise from about 0.1% to about 20%, specifically from about 0.5% to about 10%, and more specifically from about 0.5% to about 5% by weight of the personal care composition. Such polymers comprise polyorganosiloxane polymers crosslinked by a crosslinking agent. Suitable crosslinking agents are disclosed in WO98/22085. Examples of suitable polyorganosiloxane polymers for use herein include methyl vinyl dimethicone, methyl vinyl diphenyl dimethicone and methyl vinyl phenyl methyl diphenyl dimethicone.

Another class of silicone components suitable for use in a silicone oil phase herein includes polydiorganosiloxane-polyoxyalkylene copolymers containing at least one polydiorganosiloxane segment and at least one polyoxyalkylene segment. Suitable polydiorganosiloxane segments and copolymers thereof are disclosed in WO98/22085. Suitable polydiorganosiloxane-polyalkylene copolymers are available commercially under the tradename BELSIL™ from Wacker-Chemie GmbH. An example of a copolymer fluid blend for use herein includes Dow Corning DC3225C which has the CTFA designation Dimethicone/Dimethicone copolyol.

Personal care compositions of the present invention may also comprise an organic sunscreen. Suitable sunscreens can have UVA absorbing properties, UVB absorbing properties or a mixture thereof. The exact amount of the sunscreen active will vary depending upon the desired Sun Protection Factor, i.e., the "SPF" of the composition as well as the desired level of UV protection. SPF is a commonly used measure of photoprotection of a sunscreen against erythema. The SPF is defined as a ratio of the ultraviolet energy required to produce minimal erythema on protected skin to that required to produce the same minimal erythema on unprotected skin in the same individual. Amounts of the sunscreen may comprise from about 2% to about 20%, and specifically from about 4% to about 14% by weight of the personal care composition. Suitable sunscreens include, but are not limited to, those approved for use in the United States, Japan, Europe and Australia. The compositions of the present invention comprise an SPF of about 2 to about 30, specifically about 4 about 30, and more specifically about 4 to about 15.

The personal care compositions of the present invention may include one or more UVA absorbing sunscreen actives that absorb UV radiation having a wavelength of from about 320 nm to about 400 nm. Suitable UVA absorbing sunscreen actives are selected from dibenzoylmethane derivatives, anthranilate derivatives such as methylanthranilate and homomethyl, 1-N-acetylanthranilate, and mixtures thereof. Examples of dibenzoylmethane sunscreen actives are described in *Sunscreens: Development, Evaluation, and Regulatory Aspects* edited by N. J. Lowe and N. A. Shaath, Marcel Dekker, Inc (1990). The UVA absorbing sunscreen active may be present in an amount to provide broad spectrum UVA protection either independently, or in combination with, other UV protective actives which may be present in the composition.

Suitable UVA sunscreen actives are dibenzoylmethane sunscreen actives and their derivatives. They include, but are not limited to, those selected from 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-(1,1-dimethylethyl)-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4'-tert-butyl-4'- methoxydibenzoylmethane, and mixtures thereof. In one embodiment, the dibenzoyl sunscreen actives include those selected from 4-(1,1-dimethylethyl)-4'-methoxydibenzoylmethane, 4-isopropyldibenzoylmethane, and mixtures thereof. In another embodiment, the sunscreen active is 4-(1,1-dimethylethyl)-4'-methoxydibenzoylmethane.

The sunscreen active 4-(1,1-dimethylethyl)-4'-methoxydibenzoylmethane, which is also known as butyl methoxydibenzoylmethane or Avobenzone, is commercially available under the names of PARSOL® 1789 from Givaudan Roure (International) S. A. and EUSOLEX® 9020 from Merck & Co., Inc. The sunscreen 4-isoproplydibenzoylmethane, which is also known as isopropyldibenzoylmethane, is commercially available from Merck under the name of EUSOLEX® 8020.

The personal care compositions of the present invention may further include one or more UVB sunscreen actives that absorb UV radiation having a wavelength of from about 290 nm to about 320 nm. The compositions comprise an amount of the UVB sunscreen active that which is safe and effective to provide UVB protection either independently, or in combination with, other UV protective actives which may be present in the compositions. The compositions may comprise from about 0.1% to about 20%, specifically from about 0.1% to about 12%, and more specifically from about 0.5% to about 8% by weight of each UVB absorbing organic sunscreen, or as mandated by the relevant regulatory authority(s).

A variety of UVB sunscreen actives are suitable for use herein. Non-limiting examples of such organic sunscreen actives are described in U.S. Pat. No. 5,087,372 to Haffey et al; and U.S. Pat. Nos. 5,073,371 and 5,073,372 to Turner et al. Still other useful sunscreens are those disclosed in U.S. Pat. No. 4,937,370, to Sabatelli; and U.S. Pat. No. 4,999,186, to Sabatelli et al. Preferred UVB sunscreen actives are selected from 2-ethylhexyl-2-cyano-3,2-ethylhexyl N,N-dimethyl-p-aminobenzoate, p-aminobenzoic acid, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, 3-diphenylacrylate, 2-phenyl-benzimidazole-5-sulphonic acid (PBSA), cinnamate esters and their derivatives such as 2-ethylhexyl-p-methoxycinnamate and octyl-p-methoxycinnamate, salicylate esters and their derivatives such as TEA triethanolamine salicylate, ethylhexyl saliycyilate, octyldimethyl para-aminobenzoic acid-PABA, camphor derivatives and their derivatives, and mixtures thereof. Examples of organic sunscreen actives are 2-ethylhexyl-2-cyano-3,3-diphenylacrylate, 2-phenyl-benzimidazole-5-sulphonic acid (PBSA), octyl-p-methoxycinnamate, and mixtures thereof. Salt and acid neutralized forms of the acidic sunscreens are also useful herein.

An agent may also be added to any of the compositions useful in the present invention to stabilize the UVA sunscreen to prevent it from photo-degrading on exposure to UV radiation and thereby maintaining its UVA protection efficacy. A wide range of compounds have been cited as providing these stabilizing properties and should be chosen to complement both the UVA sunscreen and the composition as a whole. Suitable stabilizing agents include, but are not limited to, those described in U.S. Pat. Nos. 5,972,316; 5,968,485; 5,935,556; 5,827,508 and Published International Application WO 00/06110. Examples of stabilizing agents for use in the present invention include 2-ethylhexyl-2-cyano-3,3-diphenylacrylate, ethyl-2-cyano-3,3-diphenylacrylate, 2-ethylhexyl-3,3-diphenylacrylate, ethyl-3,3-bis (4-methoxyphenyl)acrylate, diethylhexyl 2,6 napthalate and mixtures thereof (Symrise Chemical Company).

An agent may also be added to any of the personal care compositions useful in the present invention to improve the skin substantivity of those compositions, particularly to enhance their resistance to being washed off by water or rubbed off. Examples include, but are not limited to, acrylates/$C_{12-22}$ alkylmethacrylate copolymer, acrylate/acrylate copolymer, dimethicone, dimethiconol, graft-copoly (dimethylsiloxane/iI-butyl methacrylate), lauryl dimethicone, PVP/Hexadecane copolymer, PVP/Eicosene copolymer, tricontanyl PVP and trimethoxysiloxysiliacate.

In addition to the organic sunscreens, personal care compositions of embodiments of the present invention can additionally comprise inorganic physical sunblocks. Non-limiting examples of suitable physical sunblocks are described in CTFA International Cosmetic Ingredient Dictionary, $6^{th}$ Edition, 1995, pp. 1026-28 and 1103, Sayre, R. M. et al, "Physical Sunscreens", J. Soc. Cosmet. Chem., vol 41, no 2, pp. 103-109 (1990) and Lowe et al., as per above. Specific examples of inorganic physical sunblocks are zinc oxide and titanium dioxide and mixtures thereof.

When used, the physical sunblocks are present in an amount such that the present compositions are transparent on the skin (i.e., non-whitening), from about 0.5% to about 20%, specifically from about 0.51% to about 10%, and more specifically from about 0.5% to 5% by weight of the composition. When titanium dioxide is used, it can have an anatase, rutile or amorphous structure. Manufacturers of micronized grade titanium dioxide and zinc oxide for sunscreen use include, but are not limited to Tayca Corporation, Uniqema, Shinetsu Chemical Corporation, Kerr-McGee, Nanophase, Nanosource, Sachtleben, Elementis, and BASF Corporation, as well as their distribution agents and those companies that further process the material for sunscreen use. Physical sunblock particles, e.g., titanium dioxide and zinc oxide, can be uncoated or coated with a variety of materials including but not limited to amino acids, aluminium compounds such as alumina, aluminium stearate, aluminium laurate, and the like; carboxylic acids and their salts e.g., stearic acid and its salts; phospholipids, such as lecithin; organic silicon compounds; inorganic silicon compounds such as silica and silicates and mixtures thereof. The personal care compositions of the present invention may comprise from about 0.1% to about 15%, specifically from about 0.1% to about 7% and more specifically from about 0.5% to about 5% by weight of an inorganic sunscreen.

The personal care compositions of the present invention may also include preservatives. Such preservatives include, but are not limited to pentylene glycol, ethylene diamine tetra acetate (also known as EDTA) and its salts, chlorhexidine (and its diacetate, dihydrochloride, digluconate derivatives), 1,1,1-trichloro-2-methyl-2-propanol, parachloro metaxylenol, polyhexamethylenebiguanide hydrochloride, dehydroacetic acid, diazolidinyl urea, 2,4-dichlorobenzyl alcohol, 4,4-dimethyl-1,3-oxazolidine, formaldehyde, glutaraldehyde, dimethylidantoin, imidazolidinyl urea, 5-chloro-2-methyl-4-isothiazolin-3-one, ortho-phenylphenol, 4-hydroxybenzoic acid and its (methyl-, ethyl-, propyl-, isopropyl-, butyl-, isobutyl-) esters (also known as parabens), salts, trichlosan, 2-phenoxyethanol, phenyl mercuric acetate, borate, nitrate, quaternium-15, salicilate, salicylic acid and its salts, calcium, sorbic acid and its salts, iodopropanyl butylcarbamate, calcium sorbate, zinc pyrithione, benzyl alcohol, 5-bromo-Snitro-1,3-dioxane, 2-bromo-2-nitropropane-1,3-diol, benzoic acid and its salts, sulfites, bisulfites, and benzalkonium chloride, phenoxyethanol and chloroxylenol, diazolidinyl urea, methylparaben, propylparaben, PG, isopropylparabens, isobutylparabens, butylparabens, ethylparaben, phenoxyethanol.

A variety of optional ingredients such as neutralizing agents, perfumes and perfume solubilizing agents, and coloring agents, can also be added to the personal care compositions herein. Any additional ingredients should enhance the product, for example, the skin softness/smoothness benefits of the product. In addition, any such ingredients should not negatively impact the aesthetic properties of the product. Neutralizing agents suitable for use in neutralizing acidic group containing hydrophilic gelling agents herein include sodium hydroxide, potassium hydroxide, ammonium hydroxide, monoethanolamine, diethanolamine, amino methyl propanol, tris-buffer and triethanolamine.

Other optional materials include any of the various functional and/or active ingredients known to those skilled in the art. (See e.g., McCutcheon's *Functional Materials*, North American and International Editions, (2003), published by MC Publishing Co.) Non-limiting examples include: keratolytic agents; water-soluble or solubilizable preservatives specifically at a level of from about 0.1% to about 5%, such as Germall 115, methyl, ethyl, propyl and butyl esters of hydroxybenzoic acid, benzyl alcohol, DMDM hydantoin iodopropanyl butylcarbanate available under the trade name Glydant Plus from Lonza, EDTA, Euxyl (RTM) K400, Bromopol (2-bromo-2-nitropropane-1,3-diol) and phenoxypropanol; anti-bacterials such as Irgasan (RTM) and phenoxyethanol (specifically at levels of from about 0.1% to about 5%); soluble or colloidally-soluble moisturizing agents such as hyaluaronic acid and chondroitin sulfat-estarch-grafted sodium polyacrylates such as Sanwet (RTM) IM-1000, IM-1500 and IM-2500 available from Celanese Superabsorbent Materials, Portsmith, Va., USA and described in USA-A-4,076,663; vitamins such as vitamin A, vitamin C, vitamin E, vitamin K and derivatives thereof and building blocks thereof; such as phytantriol; and vitamin K and components thereof such as the fatty alcohols such as dodecatrienol; alpha and beta hydroxyacids; aloe vera; sphingosines and phytosphingosines, cholesterol; skin whitening agents; N-acetyl cysteine; colouring agents; antibacterial agents such as TCC/TCS, also known as triclosan and trichlorocarbon; perfumes and perfume solubilizers. Examples of alpha hydroxy acids include glycolic acid, lactic acid, malic acid, and citric acid (whether derived synthetically or from natural sources and whether used alone or in combination), and their esters or relevant buffered combinations such as glycolic acid in conjunction with ammonium glycolate. Other examples of alpha-hydroxy acids include: alpha-hydroxy ethanoic acid, alpha-hydroxyoctanoic acid, alpha-hydroxycaprylic acid, and hydroxycaprylic acid, mixed fruit acid, tri-alpha hydroxy fruit acids, triple fruit acid, sugar cane extract, alpha hydroxy and botanical comprise, 1-alpha hydroxy acid and glycomer in crosslinked fatty acids alpha nutrium. Specific examples of alpha hydroxy acids are glycolic acid and lactic acid. In a particular embodiment, alpha hydroxy acids are used in levels of up to about 10%.

Optional materials include pigments that, where water-insoluble, contribute to and are included in the total level of oil phase ingredients. Pigments suitable for use in the compositions of the present invention can be organic and/or inorganic. Also included within the term pigment are materials having a low color or luster, such as matte finishing agents, light scattering agents, and formulation aids such as micas, seracites, and carbonate salts. Further examples of suitable pigments are titanium dioxide, predispersed titanium dioxide, iron oxides, zinc oxide, bismuth oxychloride (whether pre-dispersed and/or pre-coated or not) coated iron oxides, ultramarine blue, D&C dyes and lakes, FD&C colors, natural color additives such as carmine, and mixtures thereof. Depending upon the type of composition, a mixture of pigments will normally be used. Exemplary pigments for use herein from the viewpoint of moisturization, skin feel, skin appearance and emulsion compatibility are treated pigments. The pigments may be treated with compounds, including but not limited to amino acids, silicones, lecithin and ester oils.

Suitably, the pH of the personal care compositions herein is in the range from about 3.5 to about 10, specifically from about 4 to about 8, and more specifically from about 5 to about 7, wherein the pH of the final composition is adjusted by addition of acidic, basic or buffer salts as necessary, depending upon the composition of the forms and the pH-requirements of the compounds.

One skilled in the art will appreciate the various techniques for preparing the personal care compositions of the present invention, any of which may be employed herein. In general the aqueous phase and/or the oil phase would be prepared separately, with materials of similar phase partitioning being added in any order. If the final product is an emulsion, the two phases will then be combined with vigorous stirring and/or homogenization as necessary to reduce the size of the internal phase droplets. Any ingredients in the formulation with high volatility, or which are susceptible to hydrolysis or decomposition at high temperatures, can be added with gentle stirring towards the end of the process, post emulsification if applicable. Dosage frequency and amount will depend upon the desired performance criteria.

In order that the invention may be more readily understood, reference is made to the following examples, which are intended to be illustrative of the invention, but are not intended to be limiting in scope.

EXAMPLES

Example 1

A. A genetically engineered silk-elastin repeat sequence protein block copolymer (SELP) was isolated and purified from *E. coli* bacteria. The *E. coli* containing a specific silk-elastin repeat sequence protein copolymer SELP47K recombinant DNA was obtained from Protein Polymer Technologies, Inc. (PPTI) of San Diego, Calif. The *E. coli* may be prepared in accordance with the methods described in U.S. Pat. Nos. 5,243,038 and 6,355,776. The recovery of kilogram quantities of SELP was also demonstrated. The silk-elastin copolymer SELP47K had a general structure of head-[(GAGAGS)$_2$(GVGVP)$_3$GKGVP(GVGP)$_4$ (GAGAGS)$_2$]$_{13}$-tail (SEQ ID NO. 19). The copolymer contained 886 amino acids, with 780 amino acids in the repeating sequence unit. The SELP47K had a molecular weight of about 70,000 Daltons, and the pI of the protein is 10.5.

Monodispersed silk-elastin protein polymer SELP47K was produced for application testing in the following manner. *E. coli* fermentation was performed to produce a cell-paste containing monodispersed SELP47K. The cell-paste was placed in ice cold water and homogenized to make the cell extract. The cell-extract was mixed with polyethyleneimine and a filter-aid and was allowed to stir at 7° C. for one hour. The polyethyeleneimine caused precipitation of cell debris and a significant amount of *E. coli* proteins. The SELP47K containing reaction mixture was then filtered using Rotary Drum Vacuum Filter (RVDF). The filtered SELP47K solution was then mixed with ammonium sulfate to 25% saturation, which led to precipitation of SELP47K. Precipitated SELP47K and mother liquor was mixed with a filter-aid and again filtered using RVDF. The RVDF cake containing SELP47K and filter-aid was mixed with cold water to dissolve the SELP47K. This precipitation and solubilization step was repeated one more time to improve the purity profile of the SELP47K. Purified monodispersed SELP47K was then water-exchanged until the conductivity of SELP solution reached 50 μS/cm$^2$. The monodispersed SELP solution was then concentrated to 10% wt/vol and then lyophilized to make powdered monodispersed SELP47K protein polymer. The material was stored at −70° C. until needed for application testing.

B. SELP variants were either obtained from PPTI or genetically engineered (Table 1).

TABLE 1

SELP variants, properties.

| Variant Name | Number of Subunits | Lysine Substitution | Molecular Weight (Da) | Isoelectric Point |
|---|---|---|---|---|
| SELP47E | 13 | Glutamic Acid | 70,212 | 4.16 |
| SELP47K-3 | 3 | none | 20,748 | 9.52 |
| SELP47R-3 | 3 | Arginine | 20,960 | 10.5 |
| SELP47E-3 | 3 | Glutamic Acid | 20,879 | 5.9 |
| SELP27K | 13 | none | 59,401 | 10.53 |
| SELP37K | 13 | none | 64,605 | 10.53 |
| SELP58 | 13 | none | 74,765 | 6.7 |
| SELP67K | 13 | none | 80,347 | 10.53 |

The E. coli strains containing a specific silk-elastin repeat sequence protein copolymer SELP47K, SELP37K and SELP27K recombinant DNA were also obtained from Protein Polymer Technologies, Inc. of San Diego, Calif. SELP67K, SELP58, SELP37K and SELP27K variant proteins were produced in 14 L fed batch culture using standard SELP47K production protocols, as described above. Proteins were purified and characterized as follows: 40 grams of cell pastes collected from 14 L cultures were lysed via French-press followed by the addition of polyethyleneimine (0.8 w/v %). Centrifugation was used to separate the cellular debris from the cell extract. SELP polymers were precipitated from the cell extract using ammonium sulfate (30% saturation), collected by centrifugation and reconstituted in water. Residual salts were removed by dialysis against water and SELP polymers were lyophilized and characterized using sodium dodecyl sulfate polyacrylamide gel electrophoresis (SDS-PAGE). SELP47K-3 species was excised from SDS-PAGE gels and further characterized, its identity confirmed, by LC-MS/MS (Liquid Chromatographic Mass Spectroscopy). The molecular weight of the intact SELP47K-3 protein was also confirmed using MALDI-TOF/MS (Matrix Assisted Laser Desorption Ionization Time of Flight Mass Spectrometry).

The protocol used for the genetic engineering of variants SELP47E, SELP47K-3, SELP47R-3, and SELP47E-3 is a modification of a commercially available kit designed to create single base pair changes in multiple sites along a particular DNA sequence (QUIKCHANGE® Multi (Site-Directed Mutagenesis Kit), Stratagene cat #200513). The standard protocol involves the construction of single direction 5' phosphorylated primers that will hybridize to plasmid template regions of interest and incorporate point mutations. Thermocycling is employed that includes a ligation reaction designed to link the multiple primers during each round of synthesis.

SELP DNA sequences are unique in that the multiple repeating subunits are identical. In order to change a single amino acid residue in all subunits a single change is effectively performed multiple times. The above protocol was further modified in that primers were designed pair-wise, complementary, thereby creating PCR amplification conditions in the thermocycling process. Amplified plasmid DNA was then used to transform E. coli cells and can be further screened and characterized for desired mutations.

Methods: Conversion of SELP Lysine Residues.

Primers were designed that direct a single base change mutation resulting in conversion of lysine residues to glutamic acids or arginines while simultaneously creating a unique restriction enzyme site at this location used for subsequent plasmid screening. 5' phosphorylated primers were made complementary, in both directions (both strands) as follows:

```
Glutamic Acid conversion:
5'-GGGAGTTGGTGTACCTGGAGAAGGTGTTCCG (SEQ ID NO. 21)

GGGGTAGG-3'

3'-CCCTCAACCACATGGACCTCTTCCACAAGGC (SEQ ID NO. 22)

CCCCATCC-5'

(A20 was converted to G20)

Arginine Conversion:
5'-GGGAGTTGGGGTACCTGGACGAGGTGTTCCG (SEQ ID NO. 23)

GGGGTAGG-3'

3'-CCCTCAACCCCATGGACCTCGAGGTGGAACC (SEQ ID NO. 24)

CCCCCATCC-5'

(G19 and T20 were converted to C and G)
```

QUIKCHANGE® Multi reaction was carried out as per the manufacturer's protocol except that both complementary primers were included. 5 μl of each reaction was used to transform TOP10 cells as per protocol (Invitrogen). 100 μl of salt optimized carbon (SOC) outgrowth were plated per reaction. Transformants were picked and grown in 5 ml LB containing 50 ppm kanamycin. Plasmid DNA was obtained from cultures using the Qiagen plasmid miniprep kit and analyzed by digestion with appropriate restriction enzymes followed by gel electrophoresis. Constructs that appeared correct were confirmed by DNA sequencing. Several rounds of the above protocol were required to obtain the SELP47E variant. In all cases this method resulted in the creation of a library consisting of variants spanning a range of subunits. This distrubution ranged from 1 to 17 subunits. SELP47E-3 and SELP47R-3 were a result of this distribution. SELP47K-3 resulted from using the above methods to convert SELP47E-3 glutamic acids back to lysines.

Successful construct plasmids were used to transform E. coli MM294 using Lauryl Bertni (LB) plates containing 50 ppm kanamycin. Single colonies were picked and grown in 60 ml TM2 (recipe)+2% glucose, 50 ppm kanamycin in 500 ml fluted Erlenmeyer flasks, 30° C., 250 rpm, 16 hrs. Cell culture was supplemented with glycerol (10% v/v), and 1.5 ml aliquots were placed in cryovials and stored at −80° C.

Random vials were tested for contamination by incubating 10 μl inoculating loopfuls on LA+1.6% skim milk plates, 37° C., for 16 hrs. Integrity of the plasmids was also confirmed using plasmid purification and analysis using restriction enzyme digestion/gel electrophoresis as well as DNA sequencing. Frozen cryovials were prepared using methods known in the art and used as seed stocks for subsequent culturing, protein production.

SELP47K-3, SELP47E-3 and SELP47R-3 variant proteins were produced in 14 L fed batch culture using standard SELP47K production protocols used above. Proteins were purified and characterized as follows: 40 grams of cell pastes collected from 14L cultures were lysed via French-press followed by the addition of polyethyleneimine (0.8 w/v %). Centrifugation was used to separate the cellular debris from the cell extract. SELP polymers were precipitated from the cell extract using ammonium sulfate (30% saturation), collected by centrifugation and reconstituted in water. Residual salts were removed by dialysis against water and SELP polymers were lyophilized and characterized using sodium dodecyl sulfate polyacrylamide gel electrophoresis (SDS-PAGE). The SELP47K-3 species was excised from SDS-PAGE gels and further characterized, its identity confirmed, by LC-MS/MS. The molecular weight of the intact SELP47K-3 protein was also confirmed using MALDI-TOF/MS.–M3H+1641, M4H+1231 of silk-elastin unit. ~5 kDa Example 2

The purification and preparation of the polydispersed SELP47K silk-elastin protein polymer for application testing was carried out in the following steps. Cell separation from the fermentation broth was done using microfiltration. A cell disruption to make a cell-extract was done using a French-press. The cell extract was separated from the cell-debris using polyethyleneimine and a filter aid. The cell extract was mixed with ammonium sulfate to 25% saturation to precipitate the silk-elastin protein polymer. The precipitated silk-elastin protein polymer was further purified by dissolving it in water and precipitating it with ammonium sulfate.

In order to prepare a polydispersed silk-elastin protein polymer, the precipitated silk-elastin protein polymer was again dissolved in water and mixed with a trace amount of protease (BPN'Y217L) (Genencor International). The protease was then inactivated and destroyed by acid treatment. The polydispersed silk-elastin protein polymer was then ultrafiltered until the silk-elastin protein polymer solution reached an electrical conductivity of 50 μS/m².

The polydispersed silk-elastin protein polymer solution was concentrated to 10 wt % and was lyophilized. The lyophilized polydisperesed silk-elastin protein polymer powder was stored at −70° C. until use. The lyophilized polydispersed silk-elastion protein was then dissolved in deionized water to a desired concentration for hair application testing.

Example 3

The purification and formation of monomeric unit of SELP47K (4920 kDA molecular weight) was carried out using monodispersed material of SELP47K produced as in Example 1. The monodispersed SELP47K was dissolved in water and was treated with endopeptidase lysC protease (Sigma Chemical Company) specific for cleaving protein at lysine residue for 30 minutes at room temperature. The lysC protease was then inactivated and destroyed by acid treatment. The monomeric unit of SELP47K was then ultrafiltered until protein polymer solution conductivity reached 50 μS/m².

Example 4

Experiments were performed to determine the isoelectric point and cloud point of SELP47K (Example 1). The isoelectric point of SELP47K was determined in the following manner. A 5 mg/ml SELP47 K solution was electophoresed using Isoelectric Focusing Electrophoresis (IEF) gel and Novex electrophoresis apparatus along with protein standards markers. Analysis of the gel revealed that SELP47K is a cationic protein with an isoelectric point of 10.4. Analysis of the IEF gels for isoelectic point determination of other RSPP examples reported in Table 1 were found to be within (+/−0.2) range.

The cloud point of SELP47K was determined in the following manner. 0.1% and 1% solutions of polydisersped SELP 47K (Example 2) were prepared in three different buffers: 50 mM acetate pH 5; 50 mM Tris pH 7; 50 mM Tris pH 9. A 0.5 M NaCl salt solution was prepared in water and salt containing solutions were prepared using this stock solution. Samples were placed in quartz cuvettes and the cloud point determination was carried out using a Cary 300 spectrophotometer equipped with a thermal program and multiple cuvettes configuration. Turbidity measurements were made at 300 nm and the temperature was varied from 20-80° C.

It was determined that increasing the concentration of SELP47K in water lowered the cloud point of the protein polymer. A 0.05% solution of protein remains soluble in water even at 80° C. However, a 1% solution has a cloud point of 70° C. It was also determined that increasing pH from 5 to 9 also has a lowering effect on the cloud point of the protein polymer in very dilute solutions. At pH 5, the 0.1% solution remained soluble even at 80° C. At pH 9, the cloud point of 0.1% protein solution droped down to 60° C. The 1% protein polymer solution showed similar cloud point of ~65° C. in the 5-9 pH range.

It was also determined that increasing the salt concentration also lowered the cloud point of the SELP47K protein polymer. In pH 5 buffer, 1% protein polymer solution has a cloud point of 75° C. However, the cloud point was 65° C. with 0.2 M salt and below 60° C. when the salt concentration was raised to 0.5 M. The presence of a high salt concentration in dilute protein solutions had more affect on the cloud point than that of a relatively less dilute solution of protein polymer. A 0.1% solution had a cloud point of 50° C. when 0.5 M NaCl was present in the solution irrespective of pH. A 1% solution with 0.5 M salt has cloud point of 55° C. irrespective of pH.

Example 5

Experiments were performed to determine the glass transition temperature (Tg) and decomposition temperature of SELP47K. (Example 1) Approximately 10 mg of SELP47K material was crimped in an aluminum (Al) pan, cooled to <−150° C., then heated to >200° C. at 10° C./min under a (helium) He atmosphere. The sample displayed an endothermic peak ranging from approximately 6 to 180° C. This initially appeared to be followed by another endothermic region and the analysis was stopped near 225° C. The sample was examined and had darkened significantly from the light golden starting color. Another sample of material was examined by TGA and found to have mass loss (~8%) from room temperature to approximately 200° C., confirming the broad endotherm observed with the first sample.

A strip pf SELP47K was examined by using a dynamic mechanical analyzer (DMA) over the range of −150 to 200° C. Three tan delta peaks were observed at −109, 70, and 189° C. The peak at 189° C. coincided with a significant drop in modulus and a step change half-height in a differential scanning calorimeter (DSC) run in the same region initially was thought to be another endotherm suggesting the Tg of the material is approximately 189° C. Another DSC sample was run, pre-heating at 100° C. for 1 hour initially to remove volatiles. The mass loss endotherm was mostly removed, and a transition at 188° C. (half-height) remained. This run was stopped and the sample cooled and examined.

Based upon the results obtained, the material has a glass transition at approximately 189° C. Since there is mass loss on heating (water loss), this transition would be for the "film" material. Material degradation also appears to start near Tg. The decomposition temperature of this SELP47K was found to be 332° C.

Example 6

Experiments were performed to determine tensile mechanical properties of SELP47K (Example 1 and 2). Samples of SELP47K were prepared by freeze-drying purified SELP47K solution. The subsequent powder was redissolved in water to a solids concentration of approximately 5, 10 or 20%. Furthermore these solutions were mixed with plasticizers to an effective concentration of 1-3%. Plasticizers included in this study were polyethylene glycol 200, glycerin, and triethanolamine. 11 milliliters of these solutions were poured into a large (6 inch square) polyethylene weigh boats and the solutions were allowed to dry either in an oven at 37° C. or room temperature for 1 to 3 days. Subsequent films were successfully peeled from the weigh boat with a spatula without any damage to the polymer film.

The films were then cut into tensile specimens using a very sharp fabric cutting wheel. The specimens were approximately 6 cm long and 2.5 cm wide. The gauge length for these samples (length of sample between tensile testing clamps) was set to 3 cm and the thickness of the sample was measured at 5 points along the gauge length using a digital thickness coating instrument. The thickness of the samples was recorded as the average of the 5 points and varied from 46.4 to 188.2 microns. Both the sample width and sample thickness were entered into an Instron Software program (Merlin) to enable it to calculate the tensile strength and tensile modulus.

The samples were loaded into the jaws of an Instron® Model 5564 apparatus making sure the gauge length was always set to 3 cm and that the sample was not under any static load or stress. The 2,500 Newton (2.5 KN) load cell was used since these samples exhibited loads between 55 and 150 Newtons at break. The results of the stress-strain measurements can be seen for four of the samples in FIG. 1. The elongation % of SELP47K was determined to be 8.4 for 20% SELP47K solution film made at room temperature (RM). The tensile strength was determined to be 65.9 megapascals (MPa), and the tensile modulus was determined to be 1716.50 MPa. The results of plastisizer-SELP47K films reveal strong correlation between concentration and mechanical properties measured. For 3% PEG200 containing SELP47K, the films elongation % reached 541. The tensile strength (MPA) and tensile strain (%) for each protein polymer tested are illustrated in Table 2.

TABLE 2a (Example 1 material)

| Protein Polymer | Tensile Strength (MPA) | Tensile Strain (%) |
| --- | --- | --- |
| SELP47K (10% sol., 37 C.) | 62.06 | 3.6 |
| SELP47K (10% sol., RM) | 62.98 | 3.5 |
| SELP47K (20% sol., 37 C.) | 74.14 | 8.6 |
| SELP47K (20% sol., RM) | 65.90 | 8.4 |
| SELP47K (05% sol., 37 C.) | 19.83 | 2.6 |
| SELP47K (05% sol., RM) | 21.43 | 2.4 |
| SELP47K (20% sol., RM) + 2% Glyerol | 27.65 | 180.5 |
| SELP47K (20% sol., RM) + 2% PEG 200 | 42.25 | 541.7 |
| SELP47K (20% sol., RM) + 1% PEG 200 | 67.84 | 7.9 |
| SELP47K (20% sol., RM) + 3% TEA | 49.65 | 87 |
| SELP47K (20% sol., RM) + 1% TEA | 54.96 | 31 |
| Nylon 6 | 50.56 | 50.6 |
| Polystyrene | 42.66 | 1.8 |
| Low Density Polyethylene | 49.98 | 375.4 |

TABLE 2b (Example 2 material)

| Protein Polymer | Tensile Strength (MPA) | Tensile strain (%) |
| --- | --- | --- |
| SELP47K (10% sol., 37 C.) | 39.34 | 6.98 |
| SELP47K (10% sol. 37 C.) + 1% glycerol | 25.12 | 15.75 |

Example 7

A SELP47K (Example 1) thin film was cast in the following manner. A 10% solution of SELP47K in water was prepared. The spin coater used for making thin film was from Special Coating Systems Inc., model number P6708-D (Indianapolis, USA). The DV-1000 program was used for spinning the film. SELP47K protein solution was poured over a 316 stainless steel plate that was placed on the spinner. The spinner was rotated at 2000 rpm for 30 seconds followed by rotation at 1000 rpm for 90 seconds. The thin film was allowed to dry for an hour and the thickness of the film was measured using a magnetometer. The average thickness of the SELP47K thin film was between 2-5 μm.

Example 8

A SELP47K (Example 1) thick film was cast in the following manner. A 10% solution of SELP47K was prepared in deionized water (DI). This solution was poured to 1 mm in height into a plastic container and was allowed to set at 37° C. or room temperature for several hours leading to the formation of films. These films averaged between about 50-200 μm in thickness.

Example 9

A SELP47K (Example 1) clear thick film was cast in the following manner. A 5% solution of SELP47K was prepared in DI water. This solution was poured to 1 mm thickness on a sheet of Saran Wrap™ kept in a shallow plastic container. This container was maintained at room temperature overnight leading to the formation of a clear thick film of SELP47K. SELP47K film made though this method yielded excellent optical transparency. No X-ray diffraction pattern was obtained from this material, and, thus, the material of this film was amorphous in nature. A 1% water solution of SELP47K when investigated though circular dichroism spectroscopy, predicted 50% random coil and 50% beta sheet structure.

Example 10

Figure 2:
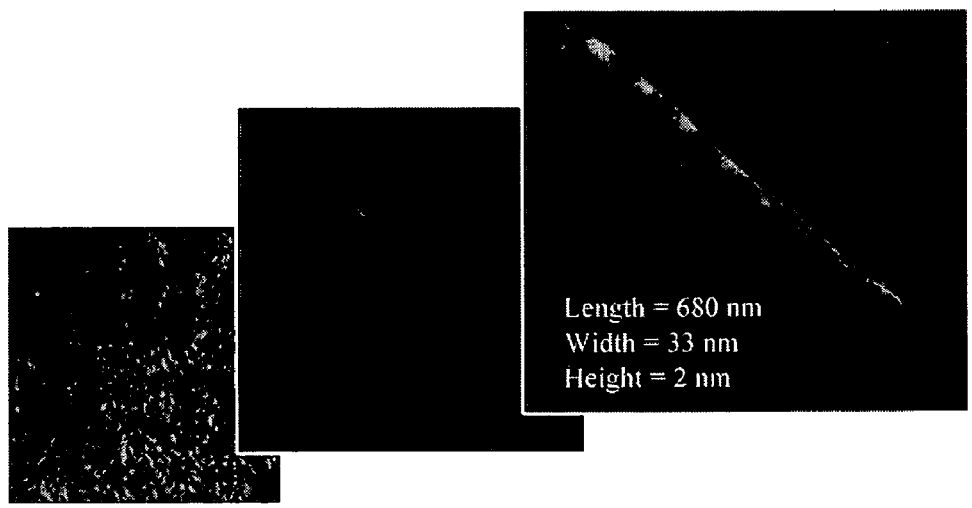
FIG. 2 illustrate AFM image of SELP 47-K film showing self assembly into nanofilaments.
Figure 3:
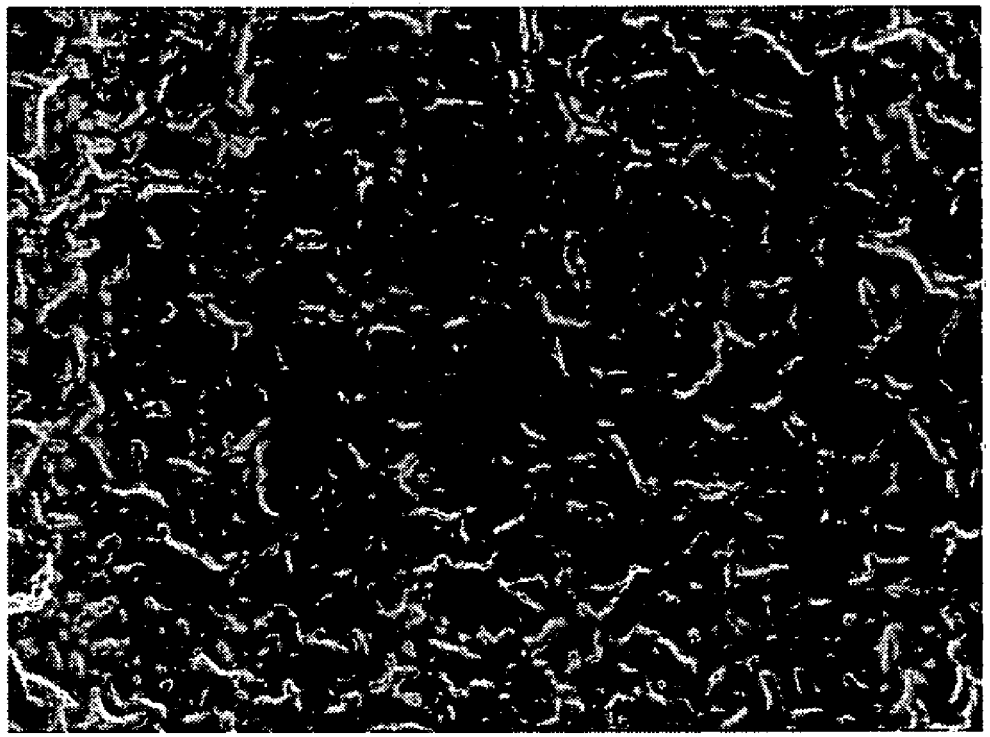
FIG. 3 illustrates SEM image of SELP 47-K film showing self assembly into nanofilaments.

Microscopy studies of SELP47K (Example 1 and 2 material) were performed. The morphology of Silk Elastin Protein (SELP47K) was characterized using various microscopy techniques including: 1) optical microscopy; 2) Field Emission Scanning Electron Microscopy (FE-SEM); and 3) Atomic Force Microscopy (AFM). Four concentrations of the SELP material (13.5%, 1.35%, 0.135% and 0.0135%) were prepared in distilled water and spin-coated on to the surface of a plasma-treated wafer (hydrophilic surface) for examination. FIGS. 2 and 3 illustrate microscopy pictures of SELP 47-K film showing self assembly into nanofilaments.

AFM and SEM examination indicated that there was a coating over the entire surface of the wafer. The coating appeared to be comprised of densely packed intertwining strands. Microscopy results indicated that the SELP47K coating, when concentrated, is comprised of densely packed, long, intertwined strands. Short, single/double strands of material were found in areas where the coating appeared to be less concentrated. Individual strands of material could be seen in the less concentrated, gray areas on the wafer. SEM analysis of the films provide the basis of water-solubility of SELP47K films. A SELP47K film made out of 10% SELP47K solution gave a water-soluble film whereas a 20% solution film was water insoluble. In 10% SELP47K solution film, micellar droplet structures were seen responsible for its water solubility whereas 20% SELP47K solution film did not have the micellar droplet structures in the film.

These strands ranged from 100 nm to 1 μm in length and 20-45 nm in diameter. These experiments confirm that SELP47K can be spun into a film and this film when studied using microscopic studies reveal that film is composed non-woven web of filaments. The film is composed of nano filaments. Nano fibers of this protein can be thus utilized in various applications, such as personal care products, due to their strength, advantage of very large surface to mass ratio and protein based targeting characteristics.

Example 11

Rinse-off conditioners were prepared. The compositions for the conditioners are set forth in Table 3.

TABLE 3

| Ingredient | Composition (Weight %) A | Composition (Weight %) B | Composition (Weight %) C |
|---|---|---|---|
| Deionized Water | q.s. to 100 | q.s. to 100 | q.s. to 100 |
| Hydroxyethylcellulose[1] | 1.5 | 1.5 | 1.5 |
| Cetearyl Alcohol[2] | 1.0 | 1.0 | 1.0 |
| PEG-100 Stearate & Glyceryl Stearate[3] | 1.0 | 1.0 | 1.0 |
| Hydrolyzed Silk Protein[4] | 5.0 | — | — |
| Hydrolyzed Elastin Protein[5] | — | 4.0 | — |
| Pure Polydisperse Silk-Elastin Protein[6] | — | — | 1.0 |
| DMDM Hydantoin[7] | 0.2 | 0.2 | 0.2 |

[1]Natrosol ® 250 MR available from Hercules of Wilmington, DE.
[2]Lanette O ® available from Cognis Corp. of Hoboken, NJ.
[3]Arlacel ® 165 available from Uniqema of Wilmington, DE.
[4]Crosilk 10,000 available from Croda of Parsippany, NJ. Equivalent weight % of protein in conditioner A is 1.0%.
[5]Crolastin available from Croda of Parsippany, NJ. Equivalent weight % of protein in conditioner B is 1.0%.
[6]Silk Elastin protein prepared in accordance with Example 2. Equivalent weight % of protein in conditioner C is 1.0%.
[7]Glydant ® available from Lonza, Inc. of Fairlawn, NJ.

In order to prepare the compositions, deionized water was added to a mixing vessel and heated to 75° C. With moderate agitation, the hydroxyethyl cellulose was dispersed until fully dissolved. The heat was decreased to 60° C. and cetearyl alcohol and PEG-100 stearate and glyceryl stearate were added. The heat was then decreased to 40° C. and then the protein for either the A, B, or C conditioner was added. The conditioner was mixed for 5-10 minutes and then DMDM hydantoin was added. The water loss was compensated for and the formulation was mixed for an additional 5 minutes. The final pH of the conditioner formulations was approximately 6-7.

Slightly bleached European human hair from International Hair Importer and Products Inc. was used for testing the conditioners in Example 3. A master hand of hair about eight inches in length was subdivided into a series of individual hair tresses. Each tress weighed about 2.5 grams. A ½ inch portion of the root end of the hair was trimmed and glued to a 2"×2" plastic tab using DUCO CEMENT®. The final weight of each tress was approximately 2.0 g. The cement was allowed to dry, and the hair tress was combed and trimmed to a length so that six inches of hair was extended below the bottom of the plastic tab. A hole was punched in middle of tab ~¼" from the top. Each tress was rinsed for 15 seconds under 40° C. tap water. Using a pipette, 1.0 g of a 9% sodium lauryl sulfate (active) solution was applied and lathered through the tress for 30 seconds. The tress was rinsed for 30 seconds under running water. Excess water was removed from the tress by passing the tress between the index and middle fingers. The tresses were placed on a tray covered with paper towels and dried overnight. Each tress was hand combed three times with the narrow teeth of an ACE® comb and evaluated using the INSTRON "WET" and the INSTRON "DRY" COMBING procedures.

For tests involving the rinse-off conditioner, the hair tress was rinsed with tap water for 15 seconds at 40° C. The test conditioner was applied to the tress in the amount of 0.8 g and the tress was stroked for 30 seconds. The tress was rinsed for 30 seconds under tap water at 40° C. The excess water was removed by pulling the tress through the index and middle fingers. The tresses were allowed to dry separately on a paper towel, overnight at room temperature. The tresses were combed once before performing the Instron study.

INSTRON COMBING is an industry recognized test for determining hair conditioning by the ease of wet combing and the ease of dry combing. The test employs an INSTRON strain gauge, which is equipped to measure the force required to comb the hair. Conditioning performance is based on the ability of a particular hair treatment formulation such as a shampoo or a hair conditioner to reduce the force required to comb the hair with the INSTRON strain gauge. The force is reported as Average Combing Load (ACL). The lower ACL value, the better the conditioning effect imparted by the formulation being tested. Typically, ACL baselines are initially established with "untreated" tresses that have only been washed with the sodium lauryl sulfate solution. The effectiveness of a treatment can be expressed as the ACL of the treated tress or the % Reduction in ACL which is calculated by ((untreated hair ACL-treated hair ACL)/untreated hair ACL)*100.

According to the INSTRON WET COMBING method, the hair was first wet by dipping it in distilled water and then the hair was detangled by combing the tress three times. The tress was then retangled by dipping in distilled water three times. The excess water was removed by passing the tress through index and middle fingers twice. The tress was then placed on the hanger and INSTRON combed. The "retangle" and "Instron combing" steps were repeated until all data points were collected. An average combing force of three tresses was measured for each treatment. The results of the INSTRON WET COMBING test conducted with the conditioners of the present invention are shown below in Table 4. Letters in the % ACL Reduction column are used to indicate that the product is superior to other designated products at a 90% confidence level. The results show that the performance of the conditioner containing the polydisperse silk elastin compound of the present invention provided a small reduction in dry combing forces compared to the conditioners that contained the hydrolyzed silk and elastin proteins. The performance of these two conditioners actually showed an increase in combing forces compared to the untreated tress.

TABLE 4

INSTRON WET COMBING

| Conditioner Tested | ACL Reduction (%)[a] |
|---|---|
| A | −22 |
| B | −32 |
| C | 3 (A, B) |

[a]Letter designations indicate that the conditioner was significantly different from the specified conditioners at a 90% confidence level According to the INSTRON DRY COMBING method, the hair was detangled by combing the tress 3 times. Then the hair was retangled by swirling the tress clockwise 3 times and counter clockwise 3 times. The tress was then placed on the hanger and INSTRON combed. The "retangle" and "Instron combing" steps were repeated until all data points were collected. An average combing force of three tresses was measured for each treatment. The results of the INSTRON DRY COMBING test conducted with the conditioners are shown below in Table 5. The results show that the performance of the silk elastin composition of the present invention provided a larger reduction in dry combing forces compared to the conditioners that contained hydrolyzed silk protein and hydrolyzed elastin proteins, respectively.

TABLE 5

INSTRON DRY COMBING

| Conditioner Tested | ACL Reduction (%)[a] |
|---|---|
| A | 20 (B) |
| B | −14 |
| C | 33 (A, B) |

[a]Letter designations indicate that the conditioner was significantly different from the specified conditioners at a 90% confidence level Example 12

Additional rinse-off conditioners were prepared. The compositions of the rinse-off conditioners are set forth in Table 6.

TABLE 6

| Ingredient | Composition (Weight %) A | Composition (Weight %) B | Composition (Weight %) C |
|---|---|---|---|
| Deionized Water | q.s. to 100 | q.s. to 100 | q.s. to 100 |
| Hydroxyethylcellulose | 1.5 | 1.5 | 1.5 |
| Cetearyl Alcohol | 1.0 | 1.0 | 1.0 |
| PEG-100 Stearate & Glyceryl Stearate | 1.0 | 1.0 | 1.0 |
| Pure Polydisperse Silk-Elastin Protein[1] | 0.01 | — | — |
| Pure Polydisperse Silk-Elastin Protein[1] | — | 0.1 | — |
| Pure Polydisperse Silk-Elastin Protein[1] | — | — | 1.0 |
| DMDM Hydantoin | 0.2 | 0.2 | 0.2 |

[1]Silk-elastin protein prepared in accordance with Example 2.

INSTRON wet and dry combing tests were performed as described in conjunction with Example 3. The Instron combing results in Tables 7 and 8 show the effect of concentration for the pure, polydisperse silk elastin protein compound. Table 8 shows that the performance of the protein material provided a reduction in dry combing force at a concentration as low as 0.1% in the rinse-off conditioner formulation, thereby improving the conditioning properties of the hair.

TABLE 7

INSTRON WET COMBING

| Conditioner Tested | ACL Reduction (%)[a] |
|---|---|
| A | −25 |
| B | −2 |
| C | 3 |

TABLE 8

INSTRON DRY COMBING

| Conditioner Tested | ACL Reduction (%)[a] |
|---|---|
| A | −5 |
| B | 11 |
| C | 33 (A) |

[a]Letter designation indicates that the conditioner is significantly different to the specified conditioner at a 95% confidence level

Example 13

Additional rinse-off conditioners were prepared. The compositions for the rinse-off conditioners are set forth in Table 9.

TABLE 9

| Ingredient | Composition (Weight %) A | Composition (Weight %) B | Composition (Weight %) C |
|---|---|---|---|
| Deionized Water | q.s. to 100 | q.s. to 100 | q.s. to 100 |
| Hydroxyethylcellulose | 1.5 | 1.5 | 1.5 |
| Cetearyl Alcohol | 1.0 | 1.0 | 1.0 |
| PEG-100 Stearate & Glyceryl Stearate | 1.0 | 1.0 | 1.0 |
| Pure Monodisperse Silk Elastin Protein[1] | 0.01 | — | — |
| Pure Monodisperse Silk Elastin Protein[1] | — | 0.1 | — |
| Pure Monodisperse Silk Elastin Protein[1] | — | — | 1.0 |
| DMDM Hydantoin | 0.2 | 0.2 | 0.2 |

[1]Silk Elasin protein prepared in accordance with Example 1.

INSTRON wet and dry combing tests were performed in conjunction with the procedures in Example 3. The Instron combing results in Tables 10 and 11 show the effect of concentration for the pure, monodispersed silk elastin protein compound. Table 11 shows that the performance of the protein material provided a small reduction in dry combing force at all concentrations in the rinse-off conditioner formulation, thereby improving the conditioning properties of the hair.

TABLE 10

INSTRON WET COMBING

| Conditioner Tested | ACL Reduction (%)[a] |
|---|---|
| A | −17 |
| B | −4 |
| C | −49 |

[a]Letter designation indicates that the conditioner was significantly different from the specified conditioner at a 95% confidence level

TABLE 11

INSTRON DRY COMBING

| Conditioner Tested | ACL Reduction (%) |
|---|---|
| A | 10 |
| B | 9 |
| C | 5 |

Example 14

The present example illustrates an efficacy study to measure changes in the biomechanical properties of skin and the ability of a single application of SELP to diminish the visual effects of aging on skin.

Eleven impaneled subjects (age 35-70 years) showing clear signs of facial skin aging were provided with a non-moisturizing soap, (Aveeno®), one week prior to study and were instructed to use the provided soap to wash the face and were required to refrain from excessive UV exposure. After a seven day conditioning phase, subjects were acclimated to the ambient temperature and humidity for thirty minutes. One side of the face of each subject was designated as the measurement side by random selection by computer. After 30-minute acclimation period, baseline digital photographs were taken, and instrumental measurements, skin replica samples and visual evaluations were made. Photographs were taken, with a Canfield Scientific Camera, of the full face, the periorbital area, and the temporal side of eye.

Chromameter (Model CR300, Minolta) measurements were taken from the periorbital area directly under the eye (Chardon et al 1991, Int. J. Cosm Science 13, 191-208). Silflo replicas (CuDerm Corporation, Dallas, Tex.) were made from the periorbital area adjacent to the temporal side of the eye (Grove et al. 1898 J. am. Acad. Dermatol. 21, 631-637 and Sun et al 1997 IFSCC Conference Mexico). Cutometer (SEM575 Courage and Khazaka, Germany) measurements were taken at the periorbital area at the upper portion of cheekbone. All measurements were performed in triplicate. An assessment of the relative depth and frequency of facial lines was performed by the method of Packman and Gans (J. Soc. Cosmet. Chem. 29, 79-90, 1978).

After baseline control data was collected, 5% SELP47K aqueous solution was applied to the face of each subject. A few drops of the SELP47K solution was dispensed onto the fingertips and smoothed into the skin of the face. Subjects were retained in the lab for 30 minutes after application of the SELP47K aqueous solution, at which point a second set of measurements were made.

Image analysis of Silflo replicas was done. Specifically, the fine line factors, which approximate the number and/or length of facial lines in the 10 evaluated bands of skin replica, were measured. At 30 minutes after application of SELP47K, fine line factors decreased by a statistically significant 13% (p=0.05). The statistical comparisons of the fine lines factors are summarized in Table 12.

TABLE 12

| | Fine Line Factors | |
|---|---|---|
| | Baseline | 30 Minutes Post Application |
| Mean | 284 | 246 |
| Variance | 1584 | 2538 |
| Observations | 11 | 11 |
| Pearson Correlation | 0.16 | |
| Hypothesized Mean Difference | 0 | |
| df | 10 | |
| t Stat | 2.18 | |
| P(T <= t) one-tail | 0.03 | |
| t Critical one-tail | 1.81 | |
| P(T <= t) two-tail | 0.05 | |
| t Critical two-tail | 2.23 | |

Evaluation of superficial facial lines was performed by an expert evaluator using the scoring method described by Packman & Gans (1988). A 7% decrease in the superficial facial line score was assessed at the 30-minute post-treatment interval compared to baseline, which was statistically significant at the 91% confidence level (p=0.09). The statistical comparisons of these measured values are summarized in Table 13.

TABLE 13

| | Superficial Facial Line Score | |
|---|---|---|
| | Baseline | 30 Minutes Post Application |
| Mean | 40 | 37 |
| Variance | 640 | 660 |
| Observations | 11 | 11 |
| Pearson Correlation | 0.98 | |
| Hypothesized Mean Difference | 0 | |
| df | 10 | |
| t Stat | 1.90 | |
| P(T <= t) one-tail | 0.04 | |
| t Critical one-tail | 1.81 | |
| P(T <= t) two-tail | 0.09 | |
| t Critical two-tail | 2.23 | |

Chromometer values for L*, a*, and b* were read and total color value, E, was calculated for each subject. The average a* value (which is directly related to the redness of the skin) decreased with statistical significance by 6% relative to baseline (p=0.024) as shown in Table 14.

TABLE 14

| | Chromameter a* Score | |
|---|---|---|
| | Baseline | 30 Minutes Post Application |
| Mean | 11.05 | 10.39 |
| Variance | 2.08 | 2.74 |
| Observations | 11 | 11 |
| Pearson Correlation | 0.86 | |
| Hypothesized Mean Difference | 0 | |
| df | 10 | |
| t Stat | 2.66 | |
| P(T <= t) one-tail | 1.20E-02 | |
| t Critical one-tail | 1.81 | |
| P(T <= t) two-tail | 2.39E-02 | |
| t Critical two-tail | 2.23 | |

Cutometer results showed an increase in Uv (a measure of viscoelasticity and delayed distention of the skin), indicating an increase in skin softness, and was assessed at a statistical confidence level of 91% (p=0.09) as shown in Table 15.

TABLE 15

| | Cutometer Uv Score | |
|---|---|---|
| | Baseline | 30 Minutes Post Application |
| Mean | 0.09 | 0.106 |
| Variance | 0.000 | 0.001 |
| Observations | 11 | 11 |
| Pearson Correlation | 0.06 | |
| Hypothesized Mean Difference | 0 | |
| df | 10 | |
| t Stat | -1.88 | |
| P(T <= t) one-tail | 0.04 | |
| t Critical one-tail | 1.81 | |

TABLE 15-continued

| | Cutometer Uv Score | |
|---|---|---|
| | Baseline | 30 Minutes Post Application |
| P(T <= t) two-tail | | 0.09 |
| t Critical two-tail | | 2.23 |

In summary, the foremost effects of a single treatment with 5% aqueous solution of SELP47K, in this limited subject test population, were reductions in both the appearance and the measured number and/or length of fine lines in the periorbital area of the face as well as an indication of improved skin softness and the evenness of tone.

Example 15

Personal care compositions comprising any of the compounds of the invention may be provided as follows:

| MOISTURIZING BODYWASH | |
|---|---|
| RAW MATERIAL (INCI Designation) | pH = 7 Amount |
| Deionized Water | QS |
| Glycerin | 4.0 |
| PEG-6 Caprylic/Capric Glycerides | 4.0 |
| Palm Kernel Fatty acids | 3.0 |
| Sodium Laureth-3 Sulfate | 45.0 |
| Cocamide MEA | 3.0 |
| Sodium Lauroamphoacetate | 25.0 |
| Soyabean Oil | 10.0 |
| Polyquaternium-10 (JR30M) | 0.70 |
| Preservative, fragrance, color | QS |
| Repeat Sequence Protein Polymer | 1000 ppm |

| BODY WASH | | | |
|---|---|---|---|
| BODY WASH RAW MATERIAL (INCI Designation) | pH 6.5 Amount | PH 7 Amount | PH 8 Amount |
| Deionized water | QS | QS | QS |
| Sodium Laureth Sulfate | 12 | 15 | 8 |
| Cocamidopropyl Betaine | 8 | 10 | 15 |
| DecylAPG Glucoside (Plantacare 2000 1) | 0 | 2 | 1 |
| Polyquaternium-10 (JR30M) | 0.25 | 0 | 0 |
| Polyquaternium-7 (Mackam 55) | 0 | 0 | 0.7 |
| Preservative, fragrance, color | QS | QS | QS |
| Repeat Sequence Protein Polymer | 250 ppm | 500 ppm | 1000 ppm |

| BODY LOTION | | | | |
|---|---|---|---|---|
| RAW MATERIAL (INCI Designation) | pH 7 Amount | pH 7 Amount | pH 7.5 Amount | pH 7 Amount |
| Deionized Water | QS | QS | QS | QS |
| Glycerine | 8 | 8 | 10 | 12 |
| Isohexadecane | 3 | 3 | 3 | 6 |
| Niacinamide | 0 | 3 | 5 | 6 |
| Isopropyl Isostearate | 3 | 3 | 3 | 3 |
| Polyacrylamide (and), Isoparaffin, (and) Laureth-7 (Sepigel 305 [2]) | 3 | 3 | 3 | 3 |
| Petrolatum | 4 | 4 | 4 | 2 |
| Nylon 12 | 2 | 2 | 2.5 | 2.5 |
| Dimethicone (DC1403 [4]) | 2 | 2 | 2.5 | 2.5 |
| Sucrose Polycottonseed Oil | 1.5 | 1.5 | 1.5 | 1.5 |
| Stearyl Alcohol 97% | 1 | 1 | 1 | 1 |
| D Panthenol | 1 | 1 | 1 | 1 |
| DL-alphaTocophero Acetate | 1 | 1 | 1 | 1 |
| Cetyl Alcohol 95% | 0.5 | 0.5 | 0.5 | 1 |
| Behenyl Alcohol | 1 | 1 | 1 | 0.5 |
| Cetearyl Alcohol (and) Cetearyl GlucosidePL 68/50 | 0.4 | 0.4 | 0.5 | 0.5 |
| Stearic Acid | 0.15 | 0.15 | 0.15 | 0.15 |
| PEG-100-Stearate (MYRJ 59 [1]) | 0.15 | 0.15 | 0.15 | 0.15 |
| Preservative, fragrance, color | QS | QS | QS | QS |
| Repeat sequence protein polymers | 250 ppm | 500 ppm | 750 ppm | 1000 ppm |

| LEAVE-ON HAIR CONDITIONER | |
|---|---|
| RAW MATERIAL (INCI Designation) | Amount |
| Deionized Water | QS |
| Isostearamidopropyl Morpholine Lactate | 6.0 |
| Hydroxyethylcellulose | 1.0 |
| Preservative, fragrance, color | QS |
| Repeat sequence protein polymers | 1000 ppm |

| CONDITIONING SHAMPOO | |
|---|---|
| RAW MATERIAL (INCI Designation) | Amount |
| Deionized Water | QS |
| Sodium Laureth Sulfate 30% | 27.0 |
| Cocamidopropyl Betaine | 3.7 |
| Coco-Glucoside (and) Glyceryl Oleate | 5.0 |
| Coco-Glucoside (and) Glycol Distearate (and) Glycerine | 3.0 |
| Guar Hydroxypropyl Trimonium Chloride | 0.1 |
| Laureth-2 | 1.55 |
| Fragrance, preservative, color | QS |
| Repeat sequence protein polymer | 1000 ppm |

| CREAM RINSE | |
|---|---|
| RAW MATERIAL (INCI Designation) | pH 4 Amount |
| Deionized Water | QS |
| Behentrimonium Chloride | 2.0 |
| Trilaureth-4 Phosphate | 1.5 |
| Cetyl alcohol | 2.0 |
| Citric acid | QS |
| Preservative, fragrance, color | QS |
| Repeat sequence protein polymer | 1000 ppm |

| NOURISHING HAIR CONDITIONER/TREATMENT | |
|---|---|
| RAW MATERIAL (INCI Designation) | pH 6 Amount |
| Deionized Water | QS |
| Behentrimonium Methosulfate (and) Cetyl Alcohol | 4.0 |
| Wheat germ oil | 1.0 |
| Cetyl alcohol | 0.5 |
| Propylene glycol | 5.0 |
| PEG-60 Lanolin | 1.0 |
| Panthenol | 2.0 |
| Lupin amino acids | 1.0 |
| Cocodimonium Hydroxypropyl Hydrolyzed Wheat Protein | 1.0 |
| Fragrance, preservative, color | QS |
| Repeat sequence protein polymer | 1000 ppm |

| ANTI-DANDRUFF SHAMPOO | |
|---|---|
| RAW MATERIAL (INCI Designation) | Amount |
| Deionized Water | QS |
| Magnesium Aluminum Silicate | 1.0 |
| Hydroxypropyl Methylcellulose | 0.8 |
| Sodium Olefin Sulfate 40% | 35.0 |
| Lauramide DEA | 4.0 |
| Soyamide DEA | 1.0 |
| Quaternium-70 Hydrolyzed Collagen | 2.0 |
| Zinc Pyrithione 40% | 4.0 |
| Fragrance, preservative, color | QS |
| Repeat sequence protein polymer | 1000 ppm |

ULTRA-HIGH MOISTURIZING FACIAL CREAM/LOTION EMULSION

| RAW MATERIAL (INCI Designation) | pH 7 Amount | pH 7 Amount |
|---|---|---|
| Deionized water | QS | QS |
| Glycerin | 12 | 5 |
| PEG 400 [6] | 0 | 10 |
| Niacinamide | 5 | 7 |
| Isohexadecane | 5 | 5 |
| Dimethicone (DC1403 [3]) | 3 | 2 |
| Polyacrylamide (and), Isoparaffin (and), Laureth-7 (Sepigel 305 [1]) | 3 | 3 |
| Isopropyl Isostearate | 2 | 2 |
| Polymethylsilsesquioxane | 2 | 2 |
| Cetyl Alcohol 95% | 1 | 1 |
| Sucrose polycottonseed oil | 1 | 1 |
| D-Panthenol | 1 | 1 |
| Vitamin E (Tocopherol Acetate) | 1 | 1 |
| Stearyl Alcohol 95% | 0.5 | 0.5 |
| Cetearyl Glucoside | 0.5 | 0.5 |
| Titanium dioxide | 0.3 | 0.3 |
| Stearic Acid | 0.15 | 0.15 |
| PEG-100-Stearate (Myrj 59 [4]) | 0.15 | 0.15 |
| Preservative, fragrance, color | QS | QS |
| Repeat sequence protein polymer | 250 ppm | 1500 ppm |

MOISTURIZSING CREAM

| RAW MATERIAL (INCI Designation) | pH 7 Amount | pH 7 Amount | pH 7.5 Amount |
|---|---|---|---|
| Deionized water | QS | QS | QS |
| Glycerine | 3 | 5 | 10 |
| Petrolatum | 3 | 3 | 0 |
| Cetyl Alcohol 95% | 1.5 | 1.5 | 1 |
| Dimethicone Copolyol (DC3225C[4]) | 2 | 2 | 2 |
| Isopropyl Palmitate | 1 | 1 | 0.5 |
| Carbopolmer 954 (Noveon) | 0.7 | 0.7 | 0.7 |
| Dimethicone (DC 200/350cs[4]) | 1 | 1 | 1 |
| Stearyl Alcohol 97% | 0.5 | 0.5 | 1 |
| Stearic acid | 0.1 | 0.1 | 0.1 |
| PEG-100-stearate (MYRJ 59 [1]) | 0.1 | 0.1 | 0.1 |
| Titanium Dioxide | 0.3 | 0.3 | 0.3 |
| Preservative, color, fragrance | QS | QS | QS |
| Repeat sequence protein polymer | 50 ppm | 250 ppm | 1000 ppm |

FACIAL CLEANSING EMULSION

| RAW MATERIAL (INCI Designation) | Amount |
|---|---|
| Water | 69.05 |
| Disodium EDTA | 0.1 |
| Glyceryl polymethacrylate (and) Propylene glycol | 1.0 |
| Glycerin | 2.0 |
| Xanthan gum | 0.5 |
| Hydroxyethyl cellulose | 0.5 |
| Tridecyl neopentanoate | 4.0 |
| Isocetyl stearate | 6.0 |
| Octyl palmitate | 8.0 |
| Glyceryl dilaurate | 4.0 |
| PEG-20 stearate | 2.0 |
| Glyceryl stearate (and) Laureth-23 | 2.0 |
| Lauryl pyrrolidone | 0.5 |

FACIAL CLEANSING EMULSION (-continued)

| RAW MATERIAL (INCI Designation) | Amount |
|---|---|
| Chamomile extract | 0.2 |
| Aloe vera (200×) | 0.05 |
| Fragrance, preservative | QS |
| Repeat sequence protein polymer | 0.1 |

SURFACTANT-BASED FACIAL CLEANSER

| RAW MATERIAL (INCI Designation) | Amount |
|---|---|
| Water | 62.55 |
| Acrylates/Steareth-20 methacrylate copolymer | 3.3 |
| Disodium EDTA | 0.05 |
| Glycerin | 2.0 |
| Glyceryl polymethacrylate (and) Propylene glycol (and) PVM/MA copolymer | 0.5 |
| Sodium laureth sulfate (30%) | 17.5 |
| Cetearyl alcohol | 1.0 |
| Shea butter | 1.0 |
| Disodium oleamido PEG-2 sulfosuccinate | 5.0 |
| Cocoamidopropyl Betaine | 3.0 |
| Sodium lauroyl sarcosinate | 1.0 |
| PEG-7 glyceryl cocoate | 1.0 |
| Isodecyl oleate | 1.5 |
| Peppermint extract | 0.25 |
| Eucalyptus extract | 0.25 |
| Fragrance, preservative, color, pH adjust | QS |
| Repeat sequence protein polymer | 0.1 |

FACIAL EXFOLIATING GEL

| RAW MATERIAL (INCI Designation) | Amount |
|---|---|
| Water | 64.39 |
| Disodium EDTA | 0.05 |
| Aloe vera (200×) | 0.01 |
| Benzophenone-4 | 0.25 |
| Propylene glycol | 1.0 |
| Acrylates/C10-30 alkyl acrylate crosspolymer (2%) | 20.0 |
| Glyceryl polymethacrylate (and) Propylene glycol | 10.0 |
| Glyceryl polymethacrylate (and) Propylene glycol (and) PVM/MA copolymer | 1.0 |
| Hydrogenated jojoba oil | 1.5 |
| Fragrance, preservative, color, pH adjust | QS |
| Repeat sequence protein polymer | 0.05 |

FACIAL TONER

| RAW MATERIAL (INCI Designation) | Amount |
|---|---|
| Water | 93.99 |
| Disodium EDTA | 0.1 |
| Butylene glycol | 2.0 |
| Aloe vera (200×) | 0.1 |
| Allantoin | 0.1 |
| Benzophenone-4 | 0.5 |
| Witch hazel extract | 0.3 |
| Propylene glycol (and) Euphrasia extract (and) Golden seal root extract (and) Green tea extract | 0.01 |
| PEG-40 hydrogenated castor oil | 0.5 |
| Quaternium-22 | 0.5 |
| Sandlewood oil | 0.02 |

FACIAL TONER

| RAW MATERIAL (INCI Designation) | Amount |
| --- | --- |
| Fragrance, preservative, color, pH adjust | QS |
| Repeat sequence protein polymer | 0.05 |

EXFOLIATING CREAM

| RAW MATERIAL (INCI Designation) | Amount |
| --- | --- |
| Water | 68.80 |
| Disodium EDTA | 0.1 |
| PVM/MA decadiene crosspolymer | 1.0 |
| Butylene glycol | 3.0 |
| PEG-20 stearate | 1.0 |
| Glyceryl stearate (and) Laureth-23 | 2.0 |
| Diisopropyl adipate | 2.0 |
| Isodecyl oleate | 2.0 |
| Isocetyl stearoyl stearate | 5.0 |
| Myristyl myristate | 1.0 |
| Glyceryl dilaurate | 2.0 |
| Sodium hydroxide, 10% | 2.6 |
| Glyceryl polymethacrylate (and) Propylene glycol | 5.0 |
| Glyceryl polymethacrylate (and) Propylene glycol (and) PVM/MA copolymer | 0.5 |
| Hydrogenated jojoba oil | 3.0 |
| Fragrance, preservative, color, pH adjust | QS |
| Repeat sequence protein polymer | 0.05 |

FACIAL MASK

| RAW MATERIAL (INCI Designation) | Amount |
| --- | --- |
| Water | 76.4 |
| Disodium EDTA | 0.1 |
| Bentonite | 12.5 |
| Potassium C12-13 Alkyl Phosphate | 5.0 |
| Propylene glycol | 4.0 |
| Sodium Coco PG-Dimonium Chloride Phosphate | 1.0 |
| Fragrance, preservative, color, pH adjust | QS |
| Repeat sequence protein polymer | 0.05 |

AFTER SHAVE BALM

| RAW MATERIAL (INCI Designation) | Amount |
| --- | --- |
| Water | 82.12 |
| Disodium EDTA | 0.1 |
| Acrylate copolymer | 2.0 |
| Acrylate/Stareth-20 methacrylate copolymer | 1.0 |
| Propylene glycol | 3.0 |
| Sodium hydroxide (10%) | 1.28 |
| Glyceryl stearate (and) Cetyl alcohol (and) Stearyl alcohol (and) Behenyl alcohol (and) Palmitic acid (and) Stearic acid (and) Hydroxyethyl cetearamidopropyldimonium chloride | 3.5 |
| Isocetyl stearate | 1.0 |
| C12-15 alkyl lactate | 1.5 |
| Octyldodecyl stearate | 3.0 |
| Glyceryl polymethacrylate (and) Propylene glycol (and) PVM/MA copolymer | 1.0 |
| Polyquaternium-11 | 0.5 |
| Fragrance, preservative, color, pH adjust | QS |
| Repeat sequence protein polymer | 0.1 |

EYE GEL

| RAW MATERIAL (INCI Designation) | Amount |
| --- | --- |
| Water | 89.14 |
| VP/Acrylates/Lauryl methacrylate copolymer | 0.5 |
| Glycerin | 5.0 |
| Aminomethyl propanol | 0.3 |
| Aloe vera (200×) | 0.05 |
| Benzophenone-4 | 0.1 |
| Glyceryl polymethacrylate (and) Propylene glycol (and) PVM/MA copolymer | 0.2 |
| Butylene glycol (and) Water (and) Witch hazel extract | 0.5 |
| Butylene glycol (and) Water (and) Cucumber extract | 0.3 |
| PEG-40 hydrogenated castor oil | 0.01 |
| Acrylates/Beheneth-25 methacrylate copolymer | 2.4 |
| Fragrance, preservative, color, pH adjust | QS |
| Repeat sequence protein polymer | 1.0 |

HIGH MELTING POINT LIPSTICK

| RAW MATERIAL (INCI Designation) | Amount |
| --- | --- |
| Ozokerite wax | 5.0 |
| Candelilla wax | 11.0 |
| Octyl dodecanol | 26.0 |
| C30-45 alkyl methicone | 5.0 |
| Cyclomethicone | 4.8 |
| Petrolatum | 3.0 |
| Lanolin oil | 9.0 |
| Avocado oil | 2.0 |
| Oleyl alcohol | 8.0 |
| Pigment/cyclomethicone | 25.0 |
| Fragrance, preservative | QS |
| Repeat sequence protein polymer | 1.0 |

LIPSTICK

| RAW MATERIAL (INCI Designation) | Amount |
| --- | --- |
| Candelilla wax | 9.1 |
| Isopropyl myristate | 9.6 |
| Lanolin | 5.0 |
| Beeswax | 4.0 |
| Paraffin (130/135) | 2.0 |
| Ozokerite wax | 2.5 |
| Castor oil | 53.7 |
| Carnauba wax | 1.5 |
| Pigments | 7.5 |
| Mineral oil | 4.0 |
| Fragrance, preservative | QS |
| Repeat sequence protein polymer | 1.0 |

LIP GLOSS

| RAW MATERIAL (INCI Designation) | Amount |
| --- | --- |
| Bis-diglyceryl polyacyladipate-1 | 43.5 |
| Bis-diglyceryl polyacyladipate-2 | 10 |
| Glycerol ricinoleate | 10 |
| Polyisobutene 1000 | 13 |
| Lanolin wax | 10 |
| Candelilla wax | 2.5 |
| Mica (and) titanium dioxide | 3 |
| d-Panthenol | 5 |

-continued

LIP GLOSS

| RAW MATERIAL (INCI Designation) | Amount |
|---|---|
| Fragrance, preservative, color | QS |
| Repeat sequence protein polymer | 1.0 |

LIP GLOSS WITH SUNSCREEN

| RAW MATERIAL (INCI Designation) | Amount |
|---|---|
| Triisostearyl Citrate | 58.4 |
| Candelilla wax | 8.0 |
| Myristyl lactate | 7.5 |
| Microcrystalline wax | 5.0 |
| Carnauba wax | 2.0 |
| Diisopropyl dimmer dilinoleate | 10.0 |
| Mica (and) Bismuth oxychloride (and) Carmine | 6.0 |
| Zinc oxide (microfine) | 2.0 |
| Fragrance, preservative | QS |
| Repeat sequence protein polymer | 1.0 |

LIP BALM

| RAW MATERIAL (INCI Designation) | Amount |
|---|---|
| Petrolatum | 47.3 |
| Isopropyl lanolate | 6.0 |
| Ozokerite wax | 16.5 |
| Candelilla wax | 4.5 |
| Diisopropyl dilinoleate | 25.0 |
| Retinyl palmitate | 0.5 |
| Tocopherol acetate | 0.2 |
| Fragrance, preservative | QS |
| Repeat sequence protein polymer | 1.0 |

WATERPROOF MASCARA

| RAW MATERIAL (INCI Designation) | Amount |
|---|---|
| Water | 49.45 |
| Propylene glycol | 3.0 |
| Triethanolamine (99%) | 3.1 |
| Acrylates/Octylacrylamine Copolymer | 5.0 |
| Diisostearoyl trimethylolpropane siloxy silicate | 5.0 |
| Candelilla wax | 4.5 |
| Beeswax | 5.5 |
| Ozokerite wax | 2.0 |
| Carnauba wax | 1.0 |
| Cetyl alcohol | 3.0 |
| Stearic acid | 5.0 |
| Iron oxides | 11.0 |
| Fragrance, preservative | QS |
| Repeat sequence protein polymer | 2.0 |

ANHYDROUS WATERPROOF MASCARA

| RAW MATERIAL (INCI Designation) | Amount |
|---|---|
| C9-11 Isoparaffin | 30.95 |
| Polyethylene | 11.0 |
| Candelilla wax | 4.5 |

-continued

ANHYDROUS WATERPROOF MASCARA

| RAW MATERIAL (INCI Designation) | Amount |
|---|---|
| Hydroxylated lanolin | 0.25 |
| Pentaerythrityl rosinate | 2.0 |
| Zinc stearate | 1.0 |
| Silica silylate | 1.0 |
| Petroleum distillates (and) Quaternium-18 hectorite (and) Propylene Carbonate | 35.0 |
| Iron oxides | 12.0 |
| Fragrance, preservative | QS |
| Repeat sequence protein polymer | 2.0 |

WATER-BASED MASCARA

| RAW MATERIAL (INCI Designation) | Amount |
|---|---|
| Water | 43.32 |
| Polyvinyl pyrrolidone (K30) | 2.0 |
| Hydroxyethyl cellulose | 1.0 |
| Triethanolamine (99%) | 2.0 |
| Disodium EDTA | 0.1 |
| Iron Oxides | 10.0 |
| Stearic acid | 4.5 |
| Glyceryl monostearate | 2.0 |
| Beeswax | 7.0 |
| Carnauba wax | 4.5 |
| Hydroxylated lanolin | 1.0 |
| Acrylates copolymer | 20.0 |
| Fragrance, preservative | QS |
| Repeat sequence protein polymer | 2.0 |

LIQUID EYELINER

| RAW MATERIAL (INCI Designation) | Amount |
|---|---|
| Water | 50-70 |
| Gellant | 0.5-1.5 |
| Wetting agent(s) | 1-3 |
| Polyol | 4-8 |
| Colorants | 10-20 |
| Alcohol | 5-10 |
| Film former | 3-8 |
| Fragrance, preservative | QS |
| Repeat sequence protein polymer | 2.0 |

NAIL ENAMEL

| RAW MATERIAL (INCI Designation) | Amount |
|---|---|
| Solvent(s) | 40-70 |
| Resin(s) | 10-20 |
| Plasticizer | 3-12 |
| Gellant | 0-2 |

NAIL ENAMEL

| RAW MATERIAL (INCI Designation) | Amount |
| --- | --- |
| Colorants | 0-3 |
| Fragrance, preservative | QS |
| Repeat sequence protein polymer | 2.0 |

CUTICLE TREATMENT

| RAW MATERIAL (INCI Designation) | Amount |
| --- | --- |
| Petrolatum | 34.8 |
| Beeswax | 7.2 |
| Ozokerite wax | 4.3 |
| Candelilla wax | 4.0 |
| Cocoa butter | 1.0 |
| Shea butter | 1.0 |
| Glyceryl dilaurate | 8.0 |
| Ethylhexyl palmitate | 20.0 |
| C12-15 alkyl lactate | 6.0 |
| PVP/Eicosene copolymer | 3.5 |
| Diisopropyl adipate | 2.0 |
| Octinoxate | 7.5 |
| Retinyl palmitate | 0.1 |
| Tocopherol acetate | 0.1 |
| Fragrance, preservative, color, pH adjust | QS |
| Repeat sequence protein polymer | 0.5 |

WATER-IN-OIL FOUNDATION

| RAW MATERIAL (INCI Designation) | Amount |
| --- | --- |
| Cyclomethicone | 12.0 |
| Dimethicone | 5.0 |
| Cyclomethicone (and) Dimethicone copolyol | 20.0 |
| Laureth-7 | 0.5 |
| Colorants (hydrophobically treated) | 2.2 |
| Titanium dioxide (and) methicone | 8.5 |
| Talc (and) methicone | 3.3 |
| Water | 37.2 |
| Sodium chloride | 2.0 |
| Propylene glycol | 8.0 |
| Fragrance, preservative | QS |
| Repeat sequence protein polymer | 1 |

ANHYDROUS MAKEUP STICK

| RAW MATERIAL (INCI Designation) | Amount |
| --- | --- |
| Ozokerite wax | 5.6 |
| Polyethylene | 5.3 |
| Glyceryl dilaurate | 5.5 |
| Isostearyl neopentanoate | 13.0 |
| Octyldodecyl stearoyl stearate | 12.0 |
| Myristyl myristate | 11.0 |
| Ethylhexyl methoxycinnamate | 7.5 |
| PVP/Eicosene copolymer | 0.5 |
| Tocopherol acetate | 0.1 |
| Dimethicone (and) Trimethylsiloxysilicate | 8.0 |
| Cyclopentasiloxane | 9.0 |
| Mica | 10.0 |
| Talc | 1.7 |
| Titanium dioxide (and) Isopropyl titanium triisostearate | 8.86 |
| Iron oxides (and) Isopropyl titanium triisostearate | 1.94 |
| Fragrance, preservative | QS |
| Repeat sequence protein polymer | 1.0 |

PRESSED POWDER FORMULATIONS

| | Loose Powder | Pressed Powder | Foundation | Blush | Eye Shadow |
| --- | --- | --- | --- | --- | --- |
| Fillers (eg. talc, mica, seracite) | 70-95 | 40-90 | 40-80 | 40-80 | 40–80 |
| Compression aids (eg. metallic soaps, waxes) | 0-2.5 | 3-5 | 2-5 | 2-7 | 2-10 |
| Texture enhancers | 10-40 | 5-40 | 10-40 | 10-40 | 0-30 |
| Colorants (eg. Iron oxides, organic colors) | 2-10 | 2-10 | 5-20 | 2-10 | 1-40 |
| Pearls (eg. Titanated mica, bismuth oxychloride) | 0-20 | 0-10 | 0-5 | 0-20 | 0-60 |
| Wet binder (eg. Octyldodecyl stearoyl stearate, di-PPG3 myristyl ether adipate, isocetyl stearate, cetyl dimethicone) | 0-3 | 2-5 | 2-5 | 3-10 | 3-15 |
| Dry binder (eg. calcium silicate, kaolin) | 0-2 | 2-5 | 2-5 | 3-8 | 3-8 |
| Fragrance, preservative | QS | QS | QS | QS | QS |
| Repeat sequence protein polymer | 2 | 2 | 2 | 2 | 2 |

WATER-IN-SILICONE FOUNDATION

| RAW MATERIAL (INCI Designation) | Amount |
| --- | --- |
| Cetyl dimethicone copolyol | 0.45 |
| Polyglycerol-4 isostearate (and) Cetyl dimethicone copolyol (and) Hexyl laurate | 1.75 |
| Polyalkylene polysiloxane copolymer | 0.9 |
| Cetyl dimethicone | 0.9 |
| Beeswax | 0.7 |
| Castor wax (and) hydrogenated castor oil | 0.35 |
| Octyl palmitate | 7.0 |
| Cyclomethicone | 7.95 |
| Phenyl trimethicone | 2.2 |
| Titanium dioxide (and) Caprylyl silane | 7.5 |
| Iron oxides (and) Caprylyl silane | 1.1 |
| Talc (and) Caprylyl silane | 3.8 |
| Cyclomethicone | 7.95 |
| Dimethicone | 1.3 |
| Water | 49.55 |
| Sodium chloride | 0.5 |
| Propylene glycol | 5.3 |
| Fragrance, preservative | QS |
| Repeat sequence protein polymer | 0.5 |

OIL-IN-WATER FOUNDATION

| RAW MATERIAL (INCI Designation) | Amount |
| --- | --- |
| Water | 59.85 |
| Polyvinylpyrrolidone | 5.0 |
| Magnesium aluminum silicate | 2.0 |
| Xanthan gum | 0.4 |
| Trisodium EDTA | 0.05 |
| Glyceryl polymethacrylate (and) Propylene glycol (and) PVM/MA copolymer | 1.0 |
| Polysorbate 20 | 1.0 |
| Kaolin | 0.8 |
| Butylene glycol | 4.0 |
| Titanium dioxide | 6.05 |
| Iron oxides | 1.15 |
| Dimethicone | 6.0 |
| Ethylhexyl palmitate | 2.0 |
| PEG/PPG-25/25 Dimethicone | 1.0 |
| Tocopherol acetate | 0.1 |
| Retinyl palmitate | 0.1 |
| Silica | 3.0 |
| Cyclopentasiloxane | 5.0 |
| Fragrance, preservative | QS |
| Repeat sequence protein polymer | 1.0 |

SUNSCREEN FORMULAS

| RAW MATERIAL (INCI Designation) | Amount | |
| --- | --- | --- |
| | SPF~25 | SPF~15 |
| Water | 52.65 | 71.10 |
| PVM/MA decadiene crosspolymer | 0.5 | 0.5 |
| Butylene glycol | 3.0 | 3.0 |
| Disodium EDTA | 0.1 | 0.1 |
| PEG-20 stearate | 1.5 | 1.5 |
| Glyceryl stearate (and) Laureth-23 | 2.0 | 2.0 |
| Isostearyl neopentanoate | 1.0 | 1.0 |
| Ethylhexyl palmitate | 2.0 | 2.0 |
| Glyceryl dilaurate | 0.5 | 0.5 |
| Octinoxate | 7.5 | 7.5 |
| Oxybenzone | 2.0 | 2.0 |
| Ethylhexyl salicylate | 3.0 | 3.0 |
| Sodium hydroxide (10%) | 1.3 | 1.3 |
| Glyceryl polymethacrylate (and) Propylene glycol | 3.0 | 3.0 |
| Glyceryl polymethacrylate (and) Propylene glycol (and) PVM/MA copolymer | 0.5 | 0.5 |
| Styrene/Acrylates copolymer (27% solids) | 18.45 | — |
| Fragrance, preservative | QS | QS |
| Repeat sequence protein polymer | 0.5 | 0.5 |

VERY WATER-RESISTANT SUNSCREEN FORMULAS

| RAW MATERIAL (INCI Designation) | Amount | |
| --- | --- | --- |
| | SPF~12 | SPF~22 |
| Water | 65.16 | 46.53 |
| Acrylates copolymer | 3.0 | 3.0 |
| Disodium EDTA | 0.1 | 0.1 |
| Butylene glycol | 2.0 | 2.0 |
| Gylceryl polymethacrylate (and) Propylene glycol (and) PVM/MA copolymer | 1.0 | 1.0 |
| Butylated PVP | 0.05 | 0.05 |
| Glyceryl stearate (and) Behenyl alcohol (and) Palmitic acid (and) Stearic acid (and) Lecithin (and) Lauryl alcohol | 4.5 | 4.5 |
| Tricontanyl PVP | 1.0 | 1.0 |
| Octyl palmitate | 2.0 | 2.0 |
| Octinoxate | 7.5 | 7.5 |
| Oxybenzone | 2.0 | 2.0 |
| Ethylhexyl salicylate | 3.0 | 3.0 |
| Tridecyl neopentanoate | 3.0 | 3.0 |
| Glyceryl dilaurate | 0.5 | 0.5 |
| Sodium hydroxide (10%) | 1.89 | 1.89 |
| Cyclopentasiloxane | 2.0 | 2.0 |
| Butylene glycol | 1.0 | 1.0 |
| Styrene/Acrylates copolymer (27% solids) | 18.45 | — |
| Fragrance, preservative | QS | QS |
| Repeat sequence protein polymer | 0.5 | 0.5 |

WATER-IN-SILICONE SUNSCREEN

| RAW MATERIAL (INCI Designation) | Amount |
| --- | --- |
| Cetyl PEG/PPG-15/15 butyl ether dimethicone | 2.0 |
| Mineral oil | 3.0 |
| Ethylhexyl palmitate | 1.0 |
| Ethylhexyl salicylate | 5.0 |
| Hydrogenated castor oil | 0.5 |
| Beeswax | 0.5 |
| Octinoxate | 7.5 |
| Polyethylene | 1.0 |
| PEG-30 dipolyhydroxystearate | 2.0 |
| Cyclopentasiloxane | 5.0 |
| Dimethicone | 5.0 |
| Sodium chloride | 0.6 |
| Acrylates/C12-22 alkylmethacrylate copolymer | 0.5 |
| Water | 66.4 |
| Fragrance, preservative | QS |
| Repeat sequence protein polymer | 0.5 |

What is claimed is:

1. A personal care composition for topical application comprising from about 0.001 weight % to about 10 weight % of the composition of a repeat sequence protein polymer and a physiologically acceptable carrier or excipient, wherein the repeat sequence protein polymer comprises SEQ ID NO. 19
wherein the personal care composition is adapted to provide at least one benefit to the surface of the skin, hair, nails, or oral cavity to which the personal care composition is topically applied.

2. The composition of claim 1, wherein the repeat sequence protein polymer comprises from about 0.01 weight % to about 5 weight % of the composition.

3. The composition of claim 1, wherein the repeat sequence protein polymer comprises from about 0.01 weight % to about 1 weight % of the composition.

4. The composition of claim 1, wherein the personal care composition comprises a hair care composition, a skin care composition, a nail care composition, a cosmetic composition, an oral care composition, or an over-the-counter pharmaceutical composition.

5. The composition of claim 4, wherein the personal care composition is a hair care composition selected from shampoo, conditioner, anti-dandruff treatment, styling aids, styling conditioner, hair repair or treatment serum, lotion, cream, pomade, and chemical treatments.

6. The composition of claim 4, wherein the personal care composition is a skin care composition selected from moisturizing body wash, body wash, antimicrobial cleanser, skin protectant cream, body lotion, facial cream, moisturizing cream, facial cleansing emulsion, surfactant-based facial cleanser, facial exfoliating gel, anti-acne treatment, facial toner, exfoliating cream, facial mask, after shave balm and sunscreen.

7. The composition of claim 4, wherein the personal care composition is a skin care composition comprises topically applied over-the-counter drugs comprising anti-fungal treatments, anti-acne treatments, skin protectants, and antiperspirants.

8. The composition of claim 4, wherein the personal care composition is a cosmetic composition comprising a makeup composition.

9. The composition of claim 4, wherein the personal care composition is a cosmetic composition selected from eye gel, high-melting point lipstick, lipstick, lip gloss, lip balm, mascara, eyeliner, pressed powder formulation and foundation.

10. The composition of claim 4, wherein the personal care composition is a nail care composition selected from nail enamel, cuticle treatment, nail polish, nail treatment, and polish remover.

11. The composition of claim 4, wherein the personal care composition is an oral care composition selected from toothpaste, mouth rinse, breath freshener, and whitening treatment.

12. The composition of claim 5, wherein the hair composition is a shampoo selected from conditioning shampoo and anti-dandruff shampoo.

13. The composition of claim 5, wherein the hair care composition is a conditioner selected from leave-on hair conditioner, cream rinse and nourishing hair conditioner treatment.

14. The composition of claim 5, wherein the hair care composition is a chemical treatment selected from permanent waves, permanent and temporary relaxers, permanent hair dyes, semi-permanent hair dyes, and temporary hair dyes.

15. The composition of claim 6, wherein the skin care composition is a sunscreen selected from non-water-resistant sunscreen, very water-resistant sunscreen and water-in-silicone sunscreen.

16. The composition of claim 9, wherein the cosmetic composition is a mascara selected from non-waterproof mascara, waterproof mascara, volumizing mascara, lengthening mascara, curling mascara, anhydrous waterproof mascara, water-based mascara, and eyelash or eyebrow treatment.

17. The composition of claim 9, wherein the cosmetic composition is a pressed powder formulation selected from loose powder, blush, eye shadow, and bronzing powder.

18. The composition of claim 9, wherein the cosmetic composition is a foundation selected from water-in-oil foundation, water-in-silicone foundation, oil-in-water foundation, anhydrous makeup stick, and cream-to-powder foundation.

19. The personal care composition as recited in claim 1, further comprising one or more compounds from the group of carriers, excipients, liposomes, active ingredients, biological or botanical products, humectants, emollients, surfactants, thickening agents, silicone components, organic sunscreens, preservatives, neutralizing agents, perfumes or pigments.

20. A process for making a personal care composition comprising combining from about 0.001 weight % to about 10 weight % of a repeat sequence protein polymer comprising SEQ ID NO. 19 with a physiologically acceptable carrier or excipient to obtain a personal care composition wherein the personal care composition is adapted to provide at least one benefit to the surface of the skin, hair, nails, or oral cavity to which the personal care composition is topically applied.

21. The process according to claim 20, further comprising combining a compound from the group of carriers, excipients, liposomes, active ingredients, humectants, emollients, surfactants, thickening agents, silicone components, organic sunscreens, preservatives, neutralizing agents, perfumes or pigments to the composition.

* * * * *

SEQUENCE LISTING

<160> NUMBER OF SEQ ID NOS: 31

<210> SEQ ID NO 1
<211> LENGTH: 6
<212> TYPE: PRT
<213> ORGANISM: Unknown
<220> FEATURE:
<223> OTHER INFORMATION: Silk-like protein

<400> SEQUENCE: 1

Ser Gly Ala Gly Ala Gly
1               5

<210> SEQ ID NO 2
<211> LENGTH: 53
<212> TYPE: PRT
<213> ORGANISM: Unknown
<220> FEATURE:
<223> OTHER INFORMATION: silk fibroin protein

<400> SEQUENCE: 2

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Ala Gly Tyr
    50

<210> SEQ ID NO 3
<211> LENGTH: 5
<212> TYPE: PRT
<213> ORGANISM: Unknown
<220> FEATURE:
<223> OTHER INFORMATION: Elastin-like protein

<400> SEQUENCE: 3

Gly Val Gly Val Pro
1               5

<210> SEQ ID NO 4
<211> LENGTH: 10
<212> TYPE: PRT
<213> ORGANISM: Unknown
<220> FEATURE:
<223> OTHER INFORMATION: Abductin-like protein
<220> FEATURE:
<221> NAME/KEY: MISC_FEATURE
<222> LOCATION: (10)..(10)
<223> OTHER INFORMATION: X = any amino acid

<400> SEQUENCE: 4

Gly Gly Phe Gly Gly Met Gly Gly Gly Xaa
1               5                   10

<210> SEQ ID NO 5
<211> LENGTH: 5
<212> TYPE: PRT
<213> ORGANISM: Unknown
<220> FEATURE:
<223> OTHER INFORMATION: Byssus-like protein

<400> SEQUENCE: 5

```
Gly Pro Gly Gly Gly
1               5

<210> SEQ ID NO 6
<211> LENGTH: 6
<212> TYPE: PRT
<213> ORGANISM: Unknown
<220> FEATURE:
<223> OTHER INFORMATION: Gluten-like protein

<400> SEQUENCE: 6

Pro Gly Gln Gly Gln Gln
1               5

<210> SEQ ID NO 7
<211> LENGTH: 9
<212> TYPE: PRT
<213> ORGANISM: Unknown
<220> FEATURE:
<223> OTHER INFORMATION: Gluten-like protein

<400> SEQUENCE: 7

Gly Tyr Tyr Pro Thr Ser Pro Gln Gln
1               5

<210> SEQ ID NO 8
<211> LENGTH: 3
<212> TYPE: PRT
<213> ORGANISM: Unknown
<220> FEATURE:
<223> OTHER INFORMATION: Gluten-like protein

<400> SEQUENCE: 8

Gly Gln Gln
1

<210> SEQ ID NO 9
<211> LENGTH: 28
<212> TYPE: PRT
<213> ORGANISM: Unknown
<220> FEATURE:
<223> OTHER INFORMATION: Titin-like protein

<400> SEQUENCE: 9

Pro Pro Ala Lys Val Pro Glu Val Pro Lys Pro Val Pro Glu Glu
1               5                   10                  15

Lys Val Pro Val Pro Val Pro Lys Lys Pro Glu Ala
            20                  25

<210> SEQ ID NO 10
<211> LENGTH: 12
<212> TYPE: PRT
<213> ORGANISM: Unknown
<220> FEATURE:
<223> OTHER INFORMATION: Extensin-like protein

<400> SEQUENCE: 10

Ser Pro Pro Pro Pro Ser Pro Lys Tyr Val Tyr Lys
1               5                   10

<210> SEQ ID NO 11
<211> LENGTH: 4
<212> TYPE: PRT
<213> ORGANISM: Unknown
<220> FEATURE:
<223> OTHER INFORMATION: Fibronectin-like protein
```

```
<400> SEQUENCE: 11

Arg Gly Asp Ser
 1

<210> SEQ ID NO 12
<211> LENGTH: 5
<212> TYPE: PRT
<213> ORGANISM: Unknown
<220> FEATURE:
<223> OTHER INFORMATION: Gliadin

<400> SEQUENCE: 12

Pro Gln Gln Pro Tyr
 1               5

<210> SEQ ID NO 13
<211> LENGTH: 5
<212> TYPE: PRT
<213> ORGANISM: Unknown
<220> FEATURE:
<223> OTHER INFORMATION: Glue polypeptide

<400> SEQUENCE: 13

Pro Thr Thr Thr Lys
 1               5

<210> SEQ ID NO 14
<211> LENGTH: 8
<212> TYPE: PRT
<213> ORGANISM: Unknown
<220> FEATURE:
<223> OTHER INFORMATION: Ice nucleating protein

<400> SEQUENCE: 14

Ala Gly Tyr Gly Ser Thr Gly Thr
 1               5

<210> SEQ ID NO 15
<211> LENGTH: 8
<212> TYPE: PRT
<213> ORGANISM: Unknown
<220> FEATURE:
<223> OTHER INFORMATION: Keratin

<400> SEQUENCE: 15

Tyr Gly Gly Ser Ser Gly Gly Gly
 1               5

<210> SEQ ID NO 16
<211> LENGTH: 5
<212> TYPE: PRT
<213> ORGANISM: Unknown
<220> FEATURE:
<223> OTHER INFORMATION: Keratin

<400> SEQUENCE: 16

Phe Gly Gly Gly Ser
 1               5

<210> SEQ ID NO 17
<211> LENGTH: 6
<212> TYPE: PRT
<213> ORGANISM: Unknown
<220> FEATURE:
<223> OTHER INFORMATION: Mucin

<400> SEQUENCE: 17
```

-continued

```
Thr Thr Thr Pro Asp Val
1               5
```

<210> SEQ ID NO 18
<211> LENGTH: 7
<212> TYPE: PRT
<213> ORGANISM: Unknown
<220> FEATURE:
<223> OTHER INFORMATION: RNA polymerase II

<400> SEQUENCE: 18

```
Tyr Ser Pro Thr Ser Pro Ser
1               5
```

<210> SEQ ID NO 19
<211> LENGTH: 780
<212> TYPE: PRT
<213> ORGANISM: Unknown
<220> FEATURE:
<223> OTHER INFORMATION: SELP 47K

<400> SEQUENCE: 19

```
Gly Ala Gly Ala Gly Ser Gly Ala Gly Ala Gly Ser Gly Val Gly Val
1               5                   10                  15

Pro Gly Val Gly Val Pro Gly Val Gly Val Pro Gly Lys Gly Val Pro
                20                  25                  30

Gly Val Gly Pro Gly Val Gly Pro Gly Val Gly Pro Gly Val Gly Pro
            35                  40                  45

Gly Ala Gly Ala Gly Ser Gly Ala Gly Ala Gly Ser Gly Ala Gly Ala
        50                  55                  60

Gly Ser Gly Ala Gly Ala Gly Ser Gly Val Gly Val Pro Gly Val Gly
65                  70                  75                  80

Val Pro Gly Val Gly Val Pro Gly Lys Gly Val Pro Gly Val Gly Pro
                85                  90                  95

Gly Val Gly Pro Gly Val Gly Pro Gly Val Gly Pro Gly Ala Gly Ala
            100                 105                 110

Gly Ser Gly Ala Gly Ala Gly Ser Gly Ala Gly Ala Gly Ser Gly Ala
        115                 120                 125

Gly Ala Gly Ser Gly Val Gly Val Pro Gly Val Gly Val Pro Gly Val
    130                 135                 140

Gly Val Pro Gly Lys Gly Val Pro Gly Val Gly Pro Gly Val Gly Pro
145                 150                 155                 160

Gly Val Gly Pro Gly Val Gly Pro Gly Ala Gly Ala Gly Ser Gly Ala
                165                 170                 175

Gly Ala Gly Ser Gly Ala Gly Ala Gly Ser Gly Ala Gly Ala Gly Ser
            180                 185                 190

Gly Val Gly Val Pro Gly Val Gly Val Pro Gly Val Gly Val Pro Gly
        195                 200                 205

Lys Gly Val Pro Gly Val Gly Pro Gly Val Gly Pro Gly Val Gly Pro
    210                 215                 220

Gly Val Gly Pro Gly Ala Gly Ala Gly Ser Gly Ala Gly Ala Gly Ser
225                 230                 235                 240

Gly Ala Gly Ala Gly Ser Gly Ala Gly Ala Gly Ser Gly Val Gly Val
                245                 250                 255

Pro Gly Val Gly Val Pro Gly Val Gly Val Pro Gly Lys Gly Val Pro
            260                 265                 270

Gly Val Gly Pro Gly Val Gly Pro Gly Val Gly Pro Gly Val Gly Pro
```

```
                275                 280                 285
Gly Ala Gly Ala Gly Ser Gly Ala Gly Ala Gly Ser Gly Ala Gly Ala
            290                 295                 300
Gly Ser Gly Ala Gly Ala Gly Ser Gly Val Gly Val Pro Gly Val Gly
305                 310                 315                 320
Val Pro Gly Val Gly Val Pro Gly Lys Gly Val Pro Gly Val Gly Pro
                325                 330                 335
Gly Val Gly Pro Gly Val Gly Pro Gly Val Gly Pro Gly Ala Gly Ala
            340                 345                 350
Gly Ser Gly Ala Gly Ala Gly Ser Gly Ala Gly Ala Gly Ser Gly Ala
            355                 360                 365
Gly Ala Gly Ser Gly Val Gly Val Pro Gly Val Gly Val Pro Gly Val
            370                 375                 380
Gly Val Pro Gly Lys Gly Val Pro Gly Val Gly Pro Gly Val Gly Pro
385                 390                 395                 400
Gly Val Gly Pro Gly Val Gly Pro Gly Ala Gly Ala Gly Ser Gly Ala
                405                 410                 415
Gly Ala Gly Ser Gly Ala Gly Ala Gly Ser Gly Ala Gly Ala Gly Ser
            420                 425                 430
Gly Val Gly Val Pro Gly Val Gly Val Pro Gly Val Gly Val Pro Gly
            435                 440                 445
Lys Gly Val Pro Gly Val Gly Pro Gly Val Gly Pro Gly Val Gly Pro
450                 455                 460
Gly Val Gly Pro Gly Ala Gly Ala Gly Ser Gly Ala Gly Ala Gly Ser
465                 470                 475                 480
Gly Ala Gly Ala Gly Ser Gly Ala Gly Ala Gly Ser Gly Val Gly Val
                485                 490                 495
Pro Gly Val Gly Val Pro Gly Val Gly Val Pro Gly Lys Gly Val Pro
            500                 505                 510
Gly Val Gly Pro Gly Val Gly Pro Gly Val Gly Pro Gly Val Gly Pro
            515                 520                 525
Gly Ala Gly Ala Gly Ser Gly Ala Gly Ala Gly Ser Gly Ala Gly Ala
            530                 535                 540
Gly Ser Gly Ala Gly Ala Gly Ser Gly Val Gly Val Pro Gly Val Gly
545                 550                 555                 560
Val Pro Gly Val Gly Val Pro Gly Lys Gly Val Pro Gly Val Gly Pro
                565                 570                 575
Gly Val Gly Pro Gly Val Gly Pro Gly Val Gly Pro Gly Ala Gly Ala
            580                 585                 590
Gly Ser Gly Ala Gly Ala Gly Ser Gly Ala Gly Ala Gly Ser Gly Ala
            595                 600                 605
Gly Ala Gly Ser Gly Val Gly Val Pro Gly Val Gly Val Pro Gly Val
            610                 615                 620
Gly Val Pro Gly Lys Gly Val Pro Gly Val Gly Pro Gly Val Gly Pro
625                 630                 635                 640
Gly Val Gly Pro Gly Val Gly Pro Gly Ala Gly Ala Gly Ser Gly Ala
                645                 650                 655
Gly Ala Gly Ser Gly Ala Gly Ala Gly Ser Gly Ala Gly Ala Gly Ser
            660                 665                 670
Gly Val Gly Val Pro Gly Val Gly Val Pro Gly Val Gly Val Pro Gly
            675                 680                 685
Lys Gly Val Pro Gly Val Gly Pro Gly Val Gly Pro Gly Val Gly Pro
690                 695                 700
```

```
Gly Val Gly Pro Gly Ala Gly Ala Gly Ser Gly Ala Gly Ala Gly Ser
705                 710                 715                 720

Gly Ala Gly Ala Gly Ser Gly Ala Gly Ala Gly Ser Gly Val Gly Val
            725                 730                 735

Pro Gly Val Gly Val Pro Gly Val Gly Val Pro Gly Lys Gly Val Pro
        740                 745                 750

Gly Val Gly Pro Gly Val Gly Pro Gly Val Gly Pro Gly Val Gly Pro
        755                 760                 765

Gly Ala Gly Ala Gly Ser Gly Ala Gly Ala Gly Ser
    770                 775                 780

<210> SEQ ID NO 20
<211> LENGTH: 3
<212> TYPE: PRT
<213> ORGANISM: Unknown
<220> FEATURE:
<223> OTHER INFORMATION: Abductin-like protein
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = any amino acid

<400> SEQUENCE: 20

Gly Xaa Xaa
1

<210> SEQ ID NO 21
<211> LENGTH: 39
<212> TYPE: DNA
<213> ORGANISM: Unknown
<220> FEATURE:
<223> OTHER INFORMATION: Primer 5' to 3' Glutamic Acid conversion

<400> SEQUENCE: 21
gggagttggt gtacctggag aaggtgttcc gggggtagg                        39

<210> SEQ ID NO 22
<211> LENGTH: 39
<212> TYPE: DNA
<213> ORGANISM: Unknown
<220> FEATURE:
<223> OTHER INFORMATION: Primer 3' to 5' Glutamic Acid conversion

<400> SEQUENCE: 22
ccctcaacca catggacctc ttccacaagg cccccatcc                        39

<210> SEQ ID NO 23
<211> LENGTH: 39
<212> TYPE: DNA
<213> ORGANISM: Unknown
<220> FEATURE:
<223> OTHER INFORMATION: Primer 5' to 3' Arginine Conversion

<400> SEQUENCE: 23
gggagttggg gtacctggac gaggtgttcc gggggtagg                        39

<210> SEQ ID NO 24
<211> LENGTH: 39
<212> TYPE: DNA
<213> ORGANISM: Unknown
<220> FEATURE:
```

-continued

<223> OTHER INFORMATION: Primer 3' to 5' Arginine Conversion

<400> SEQUENCE: 24
gggagttggg gtacctggac gaggtgttcc gggggtagg         39

<210> SEQ ID NO 25
<211> LENGTH: 884
<212> TYPE: PRT
<213> ORGANISM: Unknown
<220> FEATURE:
<223> OTHER INFORMATION: SELP 47E-13

<400> SEQUENCE: 25

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Val Gly Val Pro
        35                  40                  45

Gly Val Gly Val Pro Gly Val Gly Val Pro Gly Val Gly Val Pro Gly
    50                  55                  60

Glu Gly Val Pro Gly Val Gly Val Pro Gly Val Gly Glu Pro Gly Val
65                  70                  75                  80

Gly Val Pro Gly Ala Gly Ala Gly Ser Gly Ala Gly Ala Gly Ser Gly
                85                  90                  95

Ala Gly Ala Gly Ser Gly Ala Gly Ala Gly Ser Gly Val Gly Val Pro
            100                 105                 110

Gly Val Gly Val Pro Gly Val Gly Val Pro Gly Val Gly Val Pro Gly
        115                 120                 125

Glu Gly Val Pro Gly Val Gly Val Pro Gly Val Gly Glu Pro Gly Val
    130                 135                 140

Gly Val Pro Gly Ala Gly Ala Gly Ser Gly Ala Gly Ala Gly Ser Gly
145                 150                 155                 160

Ala Gly Ala Gly Ser Gly Ala Gly Ala Gly Ser Gly Val Gly Val Pro
                165                 170                 175

Gly Val Gly Val Pro Gly Val Gly Val Pro Gly Val Gly Val Pro Gly
            180                 185                 190

Glu Gly Val Pro Gly Val Gly Val Pro Gly Val Gly Glu Pro Gly Val
        195                 200                 205

Gly Val Pro Gly Ala Gly Ala Gly Ser Gly Ala Gly Ala Gly Ser Gly
    210                 215                 220

Ala Gly Ala Gly Ser Gly Ala Gly Ala Gly Ser Gly Val Gly Val Pro
225                 230                 235                 240

Gly Val Gly Val Pro Gly Val Gly Val Pro Gly Val Gly Val Pro Gly
                245                 250                 255

Glu Gly Val Pro Gly Val Gly Val Pro Gly Val Gly Glu Pro Gly Val
            260                 265                 270

Gly Val Pro Gly Ala Gly Ala Gly Ser Gly Ala Gly Ala Gly Ser Gly
        275                 280                 285

Ala Gly Ala Gly Ser Gly Ala Gly Ala Gly Ser Gly Val Gly Val Pro
    290                 295                 300

Gly Val Gly Val Pro Gly Val Gly Val Pro Gly Val Gly Val Pro Gly
305                 310                 315                 320

Glu Gly Val Pro Gly Val Gly Val Pro Gly Val Gly Glu Pro Gly Val
                325                 330                 335
```

```
Gly Val Pro Gly Ala Gly Ala Gly Ser Gly Ala Gly Ala Gly Ser Gly
            340                 345                 350

Ala Gly Ala Gly Ser Gly Ala Gly Ala Gly Ser Gly Val Gly Val Pro
        355                 360                 365

Gly Val Gly Val Pro Gly Val Gly Val Pro Gly Val Gly Val Pro Gly
        370                 375                 380

Glu Gly Val Pro Gly Val Gly Val Pro Gly Val Gly Glu Pro Gly Val
385                 390                 395                 400

Gly Val Pro Gly Ala Gly Ala Gly Ser Gly Ala Gly Ala Gly Ser Gly
            405                 410                 415

Ala Gly Ala Gly Ser Gly Ala Gly Ala Gly Ser Gly Val Gly Val Pro
        420                 425                 430

Gly Val Gly Val Pro Gly Val Gly Val Pro Gly Val Gly Val Pro Gly
        435                 440                 445

Glu Gly Val Pro Gly Val Gly Val Pro Gly Val Gly Glu Pro Gly Val
        450                 455                 460

Gly Val Pro Gly Ala Gly Ala Gly Ser Gly Ala Gly Ala Gly Ser Gly
465                 470                 475                 480

Ala Gly Ala Gly Ser Gly Ala Gly Ala Gly Ser Gly Val Gly Val Pro
        485                 490                 495

Gly Val Gly Val Pro Gly Val Gly Val Pro Gly Val Gly Val Pro Gly
        500                 505                 510

Glu Gly Val Pro Gly Val Gly Val Pro Gly Val Gly Glu Pro Gly Val
        515                 520                 525

Gly Val Pro Gly Ala Gly Ala Gly Ser Gly Ala Gly Ala Gly Ser Gly
        530                 535                 540

Ala Gly Ala Gly Ser Gly Ala Gly Ala Gly Ser Gly Val Gly Val Pro
545                 550                 555                 560

Gly Val Gly Val Pro Gly Val Gly Val Pro Gly Val Gly Val Pro Gly
            565                 570                 575

Glu Gly Val Pro Gly Val Gly Val Pro Gly Val Gly Glu Pro Gly Val
            580                 585                 590

Gly Val Pro Gly Ala Gly Ala Gly Ser Gly Ala Gly Ala Gly Ser Gly
        595                 600                 605

Ala Gly Ala Gly Ser Gly Ala Gly Ala Gly Ser Gly Val Gly Val Pro
        610                 615                 620

Gly Val Gly Val Pro Gly Val Gly Val Pro Gly Val Gly Val Pro Gly
625                 630                 635                 640

Glu Gly Val Pro Gly Val Gly Val Pro Gly Val Gly Glu Pro Gly Val
            645                 650                 655

Gly Val Pro Gly Ala Gly Ala Gly Ser Gly Ala Gly Ala Gly Ser Gly
            660                 665                 670

Ala Gly Ala Gly Ser Gly Ala Gly Ala Gly Ser Gly Val Gly Val Pro
        675                 680                 685

Gly Val Gly Val Pro Gly Val Gly Val Pro Gly Val Gly Val Pro Gly
        690                 695                 700

Glu Gly Val Pro Gly Val Gly Val Pro Gly Val Gly Glu Pro Gly Val
705                 710                 715                 720

Gly Val Pro Gly Ala Gly Ala Gly Ser Gly Ala Gly Ala Gly Ser Gly
            725                 730                 735

Ala Gly Ala Gly Ser Gly Ala Gly Ala Gly Ser Gly Val Gly Val Pro
        740                 745                 750

Gly Val Gly Val Pro Gly Val Gly Val Pro Gly Val Gly Val Pro Gly
```

-continued

```
                755                 760                 765
Glu Gly Val Pro Gly Val Gly Val Pro Gly Val Gly Glu Pro Gly Val
770                 775                 780

Gly Val Pro Gly Ala Gly Ala Gly Ser Gly Ala Gly Ala Gly Ser Gly
785                 790                 795                 800

Ala Gly Ala Gly Ser Gly Ala Gly Ala Gly Ser Gly Val Gly Val Pro
                805                 810                 815

Gly Val Gly Val Pro Gly Val Gly Val Pro Gly Val Gly Val Pro Gly
                820                 825                 830

Glu Gly Val Pro Gly Val Gly Val Pro Gly Val Gly Glu Pro Gly Val
                835                 840                 845

Gly Val Pro Gly Ala Gly Ala Gly Ser Gly Ala Gly Ala Gly Ser Gly
850                 855                 860

Ala Gly Ala Met Asp Pro Gly Arg Tyr Gln Asp Leu Arg Ser His His
865                 870                 875                 880

His His His His
```

<210> SEQ ID NO 26
<211> LENGTH: 246
<212> TYPE: PRT
<213> ORGANISM: Unknown
<220> FEATURE:
<223> OTHER INFORMATION: SELP 47R-3

<400> SEQUENCE: 26

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
                20                  25                  30

Met Gly Ala Gly Ala Gly Ser Gly Ala Gly Ala Gly Ser Gly Val Gly
            35                  40                  45

Val Pro Gly Val Gly Val Pro Gly Val Gly Val Pro Gly Val Gly Val
        50                  55                  60

Pro Gly Arg Gly Val Pro Gly Val Gly Val Pro Gly Val Gly Val Pro
65                  70                  75                  80

Gly Val Gly Val Pro Gly Ala Gly Ala Gly Ser Gly Ala Gly Ala Gly
                85                  90                  95

Ser Gly Ala Gly Ala Gly Ser Gly Ala Gly Ala Gly Ser Gly Val Gly
            100                 105                 110

Val Pro Gly Val Gly Val Pro Gly Val Gly Val Pro Gly Val Gly Val
        115                 120                 125

Pro Gly Arg Gly Val Pro Gly Val Gly Val Pro Gly Val Gly Val Pro
130                 135                 140

Gly Val Gly Val Pro Gly Ala Gly Ala Gly Ser Gly Ala Gly Ala Gly
145                 150                 155                 160

Ser Gly Ala Gly Ala Gly Ser Gly Ala Gly Ala Gly Ser Gly Val Gly
            165                 170                 175

Val Pro Gly Val Gly Val Pro Gly Val Gly Val Pro Gly Val Gly Val
        180                 185                 190

Pro Gly Arg Gly Val Pro Gly Val Gly Val Pro Gly Val Gly Val Pro
195                 200                 205

Gly Val Gly Val Pro Gly Ala Gly Ala Gly Ser Gly Ala Gly Ala Gly
            210                 215                 220

Ser Gly Ala Gly Ala Met Asp Pro Gly Arg Tyr Gln Asp Leu Arg Ser
225                 230                 235                 240
```

His His His His His His
                245

<210> SEQ ID NO 27
<211> LENGTH: 244
<212> TYPE: PRT
<213> ORGANISM: Unknown
<220> FEATURE:
<223> OTHER INFORMATION: SELP 47K-3

<400> SEQUENCE: 27

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Val Gly Val Pro
        35                  40                  45

Gly Val Gly Val Pro Gly Val Gly Val Pro Gly Val Gly Val Pro Gly
    50                  55                  60

Lys Gly Val Pro Gly Val Gly Val Pro Gly Val Gly Val Pro Gly Val
65                  70                  75                  80

Gly Val Pro Gly Ala Gly Ala Gly Ser Gly Ala Gly Ala Gly Ser Gly
                85                  90                  95

Ala Gly Ala Gly Ser Gly Ala Gly Ala Gly Ser Gly Val Gly Val Pro
            100                 105                 110

Gly Val Gly Val Pro Gly Val Gly Val Pro Gly Val Gly Val Pro Gly
        115                 120                 125

Lys Gly Val Pro Gly Val Gly Val Pro Gly Val Gly Val Pro Gly Val
    130                 135                 140

Gly Val Pro Gly Ala Gly Ala Gly Ser Gly Ala Gly Ala Gly Ser Gly
145                 150                 155                 160

Ala Gly Ala Gly Ser Gly Ala Gly Ala Gly Ser Gly Val Gly Val Pro
                165                 170                 175

Gly Val Gly Val Pro Gly Val Gly Val Pro Gly Val Gly Val Pro Gly
            180                 185                 190

Lys Gly Val Pro Gly Val Gly Val Pro Gly Val Gly Val Pro Gly Val
        195                 200                 205

Gly Val Pro Gly Ala Gly Ala Gly Ser Gly Ala Gly Ala Gly Ser Gly
    210                 215                 220

Ala Gly Ala Met Asp Pro Gly Arg Tyr Gln Asp Leu Arg Ser His His
225                 230                 235                 240

His His His His

<210> SEQ ID NO 28
<211> LENGTH: 246
<212> TYPE: PRT
<213> ORGANISM: Unknown
<220> FEATURE:
<223> OTHER INFORMATION: SELP 47E-3

<400> SEQUENCE: 28

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Val Gly
        35                  40                  45

-continued

```
Val Pro Gly Val Gly Val Pro Gly Val Gly Val Pro Gly Val Gly Val
    50                  55                  60
Pro Gly Glu Gly Val Pro Gly Val Gly Val Pro Gly Val Gly Val Pro
65                  70                  75                  80
Gly Val Gly Val Pro Gly Ala Gly Ala Gly Ser Gly Ala Gly Ala Gly
                85                  90                  95
Ser Gly Ala Gly Ala Gly Ser Gly Ala Gly Ala Gly Ser Gly Val Gly
            100                 105                 110
Val Pro Gly Val Gly Val Pro Gly Val Gly Val Pro Gly Val Gly Val
        115                 120                 125
Pro Gly Glu Gly Val Pro Gly Val Gly Val Pro Gly Val Gly Val Pro
    130                 135                 140
Gly Val Gly Val Pro Gly Ala Gly Ala Gly Ser Gly Ala Gly Ala Gly
145                 150                 155                 160
Ser Gly Ala Gly Ala Gly Ser Gly Ala Gly Ala Gly Ser Gly Val Gly
                165                 170                 175
Val Pro Gly Val Gly Val Pro Gly Val Gly Val Pro Gly Val Gly Val
            180                 185                 190
Pro Gly Glu Gly Val Pro Gly Val Gly Val Pro Gly Val Gly Val Pro
        195                 200                 205
Gly Val Gly Val Pro Gly Ala Gly Ala Gly Ser Gly Ala Gly Ala Gly
    210                 215                 220
Ser Gly Ala Gly Ala Met Asp Pro Gly Arg Tyr Gln Asp Leu Arg Ser
225                 230                 235                 240
His His His His His His
                245

<210> SEQ ID NO 29
<211> LENGTH: 1063
<212> TYPE: PRT
<213> ORGANISM: Unknown
<220> FEATURE:
<223> OTHER INFORMATION: Collagen-like protein

<400> SEQUENCE: 29

Met Asp Pro Val Val Leu Gln Arg Arg Asp Trp Glu Asn Pro Gly Val
1               5                   10                  15
Thr Gln Leu Asn Arg Leu Ala Ala His Pro Pro Phe Ala Ser Asp Pro
            20                  25                  30
Met Gly Ala His Gly Pro Ala Gly Pro Lys Gly Ala His Gly Pro Ala
        35                  40                  45
Gly Pro Lys Gly Ala Gln Gly Pro Ala Gly Pro Gly Gly Ala Gln Gly
    50                  55                  60
Pro Ala Gly Pro Gly Gly Ala Gln Gly Pro Ala Gly Pro Gly Gly Ala
65                  70                  75                  80
Gln Gly Pro Ala Gly Pro Gly Gly Ala Gln Gly Pro Ala Gly Pro Gly
                85                  90                  95
Gly Ala Gln Gly Pro Ala Gly Pro Gly Gly Ala Gln Gly Pro Ala Gly
            100                 105                 110
Pro Gly Gly Ala Gln Gly Pro Ala Gly Pro Gly Gly Ala Gln Gly Pro
        115                 120                 125
Ala Gly Pro Gly Gly Ala Gln Gly Pro Ala Gly Pro Gly Gly Ala Gln
    130                 135                 140
Gly Pro Ala Gly Pro Gly Gly Ala Gln Gly Pro Ala Gly Pro Gly Gly
145                 150                 155                 160
```

-continued

```
Ala Gln Gly Pro Ala Gly Pro Gly Gly Ala Gln Gly Pro Ala Gly Pro
                165                 170                 175
Gly Gly Ala Gln Gly Pro Ala Gly Pro Gly Gly Ala Gln Gly Pro Ala
            180                 185                 190
Gly Pro Gly Gly Ala Gln Gly Pro Ala Gly Pro Gly Gly Ala Gln Gly
        195                 200                 205
Pro Ala Gly Pro Gly Gly Ala Gln Gly Pro Ala Gly Pro Gly Gly Ala
    210                 215                 220
Gln Gly Pro Ala Gly Pro Gly Gly Ala Gln Gly Pro Ala Gly Pro Gly
225                 230                 235                 240
Gly Ala Gln Gly Pro Ala Gly Pro Gly Gly Ala Gln Gly Pro Ala Gly
            245                 250                 255
Pro Gly Gly Ala Gln Gly Pro Ala Gly Pro Gly Gly Ala His Gly Pro
        260                 265                 270
Ala Gly Pro Lys Gly Ala His Gly Pro Ala Gly Pro Lys Gly Ala His
    275                 280                 285
Gly Pro Ala Gly Pro Lys Gly Ala His Gly Pro Ala Gly Pro Lys Gly
        290                 295                 300
Ala Gln Gly Pro Ala Gly Pro Gly Gly Ala Gln Gly Pro Ala Gly Pro
305                 310                 315                 320
Gly Gly Ala Gln Gly Pro Ala Gly Pro Gly Gly Ala Gln Gly Pro Ala
            325                 330                 335
Gly Pro Gly Gly Ala Gln Gly Pro Ala Gly Pro Gly Gly Ala Gln Gly
        340                 345                 350
Pro Ala Gly Pro Gly Gly Ala Gln Gly Pro Ala Gly Pro Gly Gly Ala
    355                 360                 365
Gln Gly Pro Ala Gly Pro Gly Gly Ala Gln Gly Pro Ala Gly Pro Gly
    370                 375                 380
Gly Ala Gln Gly Pro Ala Gly Pro Gly Gly Ala Gln Gly Pro Ala Gly
385                 390                 395                 400
Pro Gly Gly Ala Gln Gly Pro Ala Gly Pro Gly Gly Ala Gln Gly Pro
            405                 410                 415
Ala Gly Pro Gly Gly Ala Gln Gly Pro Ala Gly Pro Gly Gly Ala Gln
        420                 425                 430
Gly Pro Ala Gly Pro Gly Gly Ala Gln Gly Pro Ala Gly Pro Gly Gly
        435                 440                 445
Ala Gln Gly Pro Ala Gly Pro Gly Gly Ala Gln Gly Pro Ala Gly Pro
    450                 455                 460
Gly Gly Ala Gln Gly Pro Ala Gly Pro Gly Gly Ala Gln Gly Pro Ala
465                 470                 475                 480
Gly Pro Gly Gly Ala Gln Gly Pro Ala Gly Pro Gly Gly Ala Gln Gly
            485                 490                 495
Pro Ala Gly Pro Gly Gly Ala Gln Gly Pro Ala Gly Pro Gly Gly Ala
        500                 505                 510
Gln Gly Pro Ala Gly Pro Gly Gly Ala His Gly Pro Ala Gly Pro Lys
    515                 520                 525
Gly Ala His Gly Pro Ala Gly Pro Lys Gly Ala His Gly Pro Ala Gly
    530                 535                 540
Pro Lys Gly Ala His Gly Pro Ala Gly Pro Lys Gly Ala Gln Gly Pro
545                 550                 555                 560
Ala Gly Pro Gly Gly Ala Gln Gly Pro Ala Gly Pro Gly Gly Ala Gln
            565                 570                 575
```

```
Gly Pro Ala Gly Pro Gly Gly Ala Gln Gly Pro Ala Gly Pro Gly Gly
            580                 585                 590
Ala Gln Gly Pro Ala Gly Pro Gly Gly Ala Gln Gly Pro Ala Gly Pro
            595                 600                 605
Gly Gly Ala Gln Gly Pro Ala Gly Pro Gly Gly Ala Gln Gly Pro Ala
            610                 615                 620
Gly Pro Gly Gly Ala Gln Gly Pro Ala Gly Pro Gly Gly Ala Gln Gly
625                 630                 635                 640
Pro Ala Gly Pro Gly Gly Ala Gln Gly Pro Ala Gly Pro Gly Gly Ala
            645                 650                 655
Gln Gly Pro Ala Gly Pro Gly Gly Ala Gln Gly Pro Ala Gly Pro Gly
            660                 665                 670
Gly Ala Gln Gly Pro Ala Gly Pro Gly Gly Ala Gln Gly Pro Ala Gly
            675                 680                 685
Pro Gly Gly Ala Gln Gly Pro Ala Gly Pro Gly Gly Ala Gln Gly Pro
            690                 695                 700
Ala Gly Pro Gly Gly Ala Gln Gly Pro Ala Gly Pro Gly Gly Ala Gln
705                 710                 715                 720
Gly Pro Ala Gly Pro Gly Gly Ala Gln Gly Pro Ala Gly Pro Gly Gly
            725                 730                 735
Ala Gln Gly Pro Ala Gly Pro Gly Gly Ala Gln Gly Pro Ala Gly Pro
            740                 745                 750
Gly Gly Ala Gln Gly Pro Ala Gly Pro Gly Gly Ala Gln Gly Pro Ala
            755                 760                 765
Gly Pro Gly Gly Ala His Gly Pro Ala Gly Pro Lys Gly Ala His Gly
            770                 775                 780
Pro Ala Gly Pro Lys Gly Ala His Gly Pro Ala Gly Pro Lys Gly Ala
785                 790                 795                 800
His Gly Pro Ala Gly Pro Lys Gly Ala Gln Gly Pro Ala Gly Pro Gly
            805                 810                 815
Gly Ala Gln Gly Pro Ala Gly Pro Gly Gly Ala Gln Gly Pro Ala Gly
            820                 825                 830
Pro Gly Gly Ala Gln Gly Pro Ala Gly Pro Gly Gly Ala Gln Gly Pro
            835                 840                 845
Ala Gly Pro Gly Gly Ala Gln Gly Pro Ala Gly Pro Gly Gly Ala Gln
            850                 855                 860
Gly Pro Ala Gly Pro Gly Gly Ala Gln Gly Pro Ala Gly Pro Gly Gly
865                 870                 875                 880
Ala Gln Gly Pro Ala Gly Pro Gly Gly Ala Gln Gly Pro Ala Gly Pro
            885                 890                 895
Gly Gly Ala Gln Gly Pro Ala Gly Pro Gly Gly Ala Gln Gly Pro Ala
            900                 905                 910
Gly Pro Gly Gly Ala Gln Gly Pro Ala Gly Pro Gly Gly Ala Gln Gly
            915                 920                 925
Pro Ala Gly Pro Gly Gly Ala Gln Gly Pro Ala Gly Pro Gly Gly Ala
            930                 935                 940
Gln Gly Pro Ala Gly Pro Gly Gly Ala Gln Gly Pro Ala Gly Pro Gly
945                 950                 955                 960
Gly Ala Gln Gly Pro Ala Gly Pro Gly Gly Ala Gln Gly Pro Ala Gly
            965                 970                 975
Pro Gly Gly Ala Gln Gly Pro Ala Gly Pro Gly Gly Ala Gln Gly Pro
            980                 985                 990
Ala Gly Pro Gly Gly Ala Gln Gly  Pro Ala Gly Pro Gly  Gly Ala Gln
```

```
                    995              1000              1005
Gly Pro  Ala Gly Pro Gly  Gly Ala Gln Gly Pro  Ala Gly Pro Gly
         1010              1015              1020

Gly Ala  His Gly Pro Ala  Gly Pro Lys Gly Ala  His Gly Pro Ala
         1025              1030              1035

Gly Pro  Lys Met Asp Pro  Gly Arg Tyr Gln Leu  Ser Ala Gly Arg
         1040              1045              1050

Tyr His  Tyr Gln Leu Val  Trp Cys Gln Lys
         1055              1060

<210> SEQ ID NO 30
<211> LENGTH: 1038
<212> TYPE: PRT
<213> ORGANISM: Unknown
<220> FEATURE:
<223> OTHER INFORMATION: SELP 67K

<400> SEQUENCE: 30

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Val Gly Val Pro Gly Val Gly Val Pro Gly Val Gly Val Pro
        35                  40                  45

Gly Val Gly Val Pro Gly Lys Gly Val Pro Gly Val Gly Val Pro Gly
    50                  55                  60

Val Gly Val Pro Gly Val Gly Val Pro Gly Ala Gly Ala Gly Ser Gly
65                  70                  75                  80

Ala Gly Ala Gly Ser Gly Ala Gly Ala Gly Ser Gly Ala Gly Ala Gly
                85                  90                  95

Ser Gly Ala Gly Ala Gly Ser Gly Ala Gly Ala Gly Ser Gly Val Gly
            100                 105                 110

Val Pro Gly Val Gly Val Pro Gly Val Gly Val Pro Gly Val Gly Val
        115                 120                 125

Pro Gly Lys Gly Val Pro Gly Val Gly Val Pro Gly Val Gly Val Pro
    130                 135                 140

Gly Val Gly Val Pro Gly Ala Gly Ala Gly Ser Gly Ala Gly Ala Gly
145                 150                 155                 160

Ser Gly Ala Gly Ala Gly Ser Gly Ala Gly Ala Gly Ser Gly Ala Gly
                165                 170                 175

Ala Gly Ser Gly Ala Gly Ala Gly Ser Gly Val Gly Val Pro Gly Val
            180                 185                 190

Gly Val Pro Gly Val Gly Val Pro Gly Val Gly Val Pro Gly Lys Gly
        195                 200                 205

Val Pro Gly Val Gly Val Pro Gly Val Gly Val Pro Gly Val Gly Val
    210                 215                 220

Pro Gly Ala Gly Ala Gly Ser Gly Ala Gly Ala Gly Ser Gly Ala Gly
225                 230                 235                 240

Ala Gly Ser Gly Ala Gly Ala Gly Ser Gly Ala Gly Ala Gly Ser Gly
                245                 250                 255

Ala Gly Ala Gly Ser Gly Val Gly Val Pro Gly Val Gly Val Pro Gly
            260                 265                 270

Val Gly Val Pro Gly Val Gly Val Pro Gly Lys Gly Val Pro Gly Val
        275                 280                 285

Gly Val Pro Gly Val Gly Val Pro Gly Val Gly Val Pro Gly Ala Gly
```

```
            290                 295                 300
Ala Gly Ser Gly Ala Gly Ala Gly Ser Gly Ala Gly Ser Gly
305                 310                 315                 320
Ala Gly Ala Gly Ser Gly Ala Gly Ala Gly Ser Gly Ala Gly
                325                 330                 335
Ser Gly Val Gly Val Pro Gly Val Gly Val Pro Gly Val Pro
            340                 345                 350
Gly Val Gly Val Pro Gly Lys Gly Val Pro Gly Val Gly Val Pro Gly
            355                 360                 365
Val Gly Val Pro Gly Val Gly Val Pro Gly Ala Gly Ala Gly Ser Gly
            370                 375                 380
Ala Gly Ala Gly Ser Gly Ala Gly Ala Gly Ser Gly Ala Gly Ala Gly
385                 390                 395                 400
Ser Gly Ala Gly Ala Gly Ser Gly Ala Gly Ala Gly Ser Gly Val Gly
                405                 410                 415
Val Pro Gly Val Gly Val Pro Gly Val Gly Val Pro Gly Val Gly Val
            420                 425                 430
Pro Gly Lys Gly Val Pro Gly Val Gly Val Pro Gly Val Gly Val Pro
            435                 440                 445
Gly Val Gly Val Pro Gly Ala Gly Ala Gly Ser Gly Ala Gly Ala Gly
            450                 455                 460
Ser Gly Ala Gly Ala Gly Ser Gly Ala Gly Ala Gly Ser Gly Ala Gly
465                 470                 475                 480
Ala Gly Ser Gly Ala Gly Ala Gly Ser Gly Val Gly Val Pro Gly Val
                485                 490                 495
Gly Val Pro Gly Val Gly Val Pro Gly Val Gly Val Pro Gly Lys Gly
            500                 505                 510
Val Pro Gly Val Gly Val Pro Gly Val Gly Val Pro Gly Val Gly Val
            515                 520                 525
Pro Gly Ala Gly Ala Gly Ser Gly Ala Gly Ala Gly Ser Gly Ala Gly
            530                 535                 540
Ala Gly Ser Gly Ala Gly Ala Gly Ser Gly Ala Gly Ala Gly Ser Gly
545                 550                 555                 560
Ala Gly Ala Gly Ser Gly Val Gly Val Pro Gly Val Gly Val Pro Gly
                565                 570                 575
Val Gly Val Pro Gly Val Gly Val Pro Gly Lys Gly Val Pro Gly Val
            580                 585                 590
Gly Val Pro Gly Val Gly Val Pro Gly Val Gly Val Pro Gly Ala Gly
            595                 600                 605
Ala Gly Ser Gly Ala Gly Ala Gly Ser Gly Ala Gly Ala Gly Ser Gly
            610                 615                 620
Ala Gly Ala Gly Ser Gly Ala Gly Ala Gly Ser Gly Ala Gly Ala Gly
625                 630                 635                 640
Ser Gly Val Gly Val Pro Gly Val Gly Val Pro Gly Val Gly Val Pro
                645                 650                 655
Gly Val Gly Val Pro Gly Lys Gly Val Pro Gly Val Gly Val Pro Gly
            660                 665                 670
Val Gly Val Pro Gly Val Gly Val Pro Gly Ala Gly Ala Gly Ser Gly
            675                 680                 685
Ala Gly Ala Gly Ser Gly Ala Gly Ala Gly Ser Gly Ala Gly Ala Gly
            690                 695                 700
Ser Gly Ala Gly Ala Gly Ser Gly Ala Gly Ala Gly Ser Gly Val Gly
705                 710                 715                 720
```

-continued

Val Pro Gly Val Gly Val Pro Gly Val Gly Val Pro Gly Val Gly Val
              725                 730                 735

Pro Gly Lys Gly Val Pro Gly Val Gly Val Pro Gly Val Gly Val Pro
              740                 745                 750

Gly Val Gly Val Pro Gly Ala Gly Ala Gly Ser Gly Ala Gly Ala Gly
              755                 760                 765

Ser Gly Ala Gly Ala Gly Ser Gly Ala Gly Ala Gly Ser Gly Ala Gly
              770                 775                 780

Ala Gly Ser Gly Ala Gly Ala Gly Ser Gly Val Gly Val Pro Gly Val
785                 790                 795                 800

Gly Val Pro Gly Val Gly Val Pro Gly Val Gly Val Pro Gly Lys Gly
              805                 810                 815

Val Pro Gly Val Gly Val Pro Gly Val Gly Val Pro Gly Val Gly Val
              820                 825                 830

Pro Gly Ala Gly Ala Gly Ser Gly Ala Gly Ala Gly Ser Gly Ala Gly
              835                 840                 845

Ala Gly Ser Gly Ala Gly Ala Gly Ser Gly Ala Gly Ala Gly Ser Gly
850                 855                 860

Ala Gly Ala Gly Ser Gly Val Gly Val Pro Gly Val Gly Val Pro Gly
865                 870                 875                 880

Val Gly Val Pro Gly Val Gly Val Pro Gly Lys Gly Val Pro Gly Val
              885                 890                 895

Gly Val Pro Gly Val Gly Val Pro Gly Val Gly Val Pro Gly Ala Gly
              900                 905                 910

Ala Gly Ser Gly Ala Gly Ala Gly Ser Gly Ala Gly Ala Gly Ser Gly
              915                 920                 925

Ala Gly Ala Gly Ser Gly Ala Gly Ala Gly Ser Gly Ala Gly Ala Gly
              930                 935                 940

Ser Gly Val Gly Val Pro Gly Val Gly Val Pro Gly Val Gly Val Pro
945                 950                 955                 960

Gly Val Gly Val Pro Gly Lys Gly Val Pro Gly Val Gly Val Pro Gly
              965                 970                 975

Val Gly Val Pro Gly Val Gly Val Pro Gly Ala Gly Ala Gly Ser Gly
              980                 985                 990

Ala Gly Ala Gly Ser Gly Ala Gly Ala Gly Ser Gly Ala Gly Ala Gly
              995                1000                1005

Ser Gly Ala Gly Ala Gly Ser Gly Ala Gly Ala Gly Ser Met Asp
              1010                1015                1020

Pro Gly Arg Tyr Gln Asp Leu Arg Ser His His His His His His
              1025                1030                1035

<210> SEQ ID NO 31
<211> LENGTH: 965
<212> TYPE: PRT
<213> ORGANISM: Unknown
<220> FEATURE:
<223> OTHER INFORMATION: SELP 58

<400> SEQUENCE: 31

Met Asp Pro Val Val Leu Gln Arg Arg Asp Trp Glu Asn Pro Gly Val
1               5                  10                  15

Thr Gln Leu Asn Arg Leu Ala Ala His Pro Pro Phe Ala Ser Asp Pro
             20                  25                  30

Met Gly Val Gly Val Pro Gly Val Gly Val Pro Gly Val Gly Val Pro
             35                  40                  45

```
Gly Val Gly Val Pro Gly Val Gly Val Pro Gly Val Gly Val Pro Gly
         50                  55                  60
Val Gly Val Pro Gly Val Gly Val Pro Gly Ala Gly Ala Gly Ser Gly
 65                  70                  75                  80
Ala Gly Ala Gly Ser Gly Ala Gly Ala Gly Ser Gly Ala Gly Ala Gly
                 85                  90                  95
Ser Gly Ala Gly Ala Gly Ser Gly Val Gly Val Pro Gly Val Gly Val
                100                 105                 110
Pro Gly Val Gly Val Pro Gly Val Gly Val Pro Gly Val Gly Val Pro
            115                 120                 125
Gly Val Gly Val Pro Gly Val Gly Val Pro Gly Val Gly Val Pro Gly
        130                 135                 140
Ala Gly Ala Gly Ser Gly Ala Gly Ala Gly Ser Gly Ala Gly Ala Gly
145                 150                 155                 160
Ser Gly Ala Gly Ala Gly Ser Gly Ala Gly Ala Gly Ser Gly Val Gly
                165                 170                 175
Val Pro Gly Val Gly Val Pro Gly Val Gly Val Pro Gly Val Gly Val
            180                 185                 190
Pro Gly Val Gly Val Pro Gly Val Gly Val Pro Gly Val Gly Val Pro
        195                 200                 205
Gly Val Gly Val Pro Gly Ala Gly Ala Gly Ser Gly Ala Gly Ala Gly
    210                 215                 220
Ser Gly Ala Gly Ala Gly Ser Gly Ala Gly Ala Gly Ser Gly Ala Gly
225                 230                 235                 240
Ala Gly Ser Gly Val Gly Val Pro Gly Val Gly Val Pro Gly Val Gly
            245                 250                 255
Val Pro Gly Val Gly Val Pro Gly Val Gly Val Pro Gly Val Gly Val
        260                 265                 270
Pro Gly Val Gly Val Pro Gly Val Gly Val Pro Gly Ala Gly Ala Gly
    275                 280                 285
Ser Gly Ala Gly Ala Gly Ser Gly Ala Gly Ala Gly Ser Gly Ala Gly
290                 295                 300
Ala Gly Ser Gly Ala Gly Ala Gly Ser Gly Val Gly Val Pro Gly Val
305                 310                 315                 320
Gly Val Pro Gly Val Gly Val Pro Gly Val Gly Val Pro Gly Val Gly
            325                 330                 335
Val Pro Gly Val Gly Val Pro Gly Val Gly Val Pro Gly Val Gly Val
        340                 345                 350
Pro Gly Ala Gly Ala Gly Ser Gly Ala Gly Ala Gly Ser Gly Ala Gly
    355                 360                 365
Ala Gly Ser Gly Ala Gly Ala Gly Ser Gly Ala Gly Ala Gly Ser Gly
    370                 375                 380
Val Gly Val Pro Gly Val Gly Val Pro Gly Val Gly Val Pro Gly Val
385                 390                 395                 400
Gly Val Pro Gly Val Gly Val Pro Gly Val Gly Val Pro Gly Val Gly
            405                 410                 415
Val Pro Gly Val Gly Val Pro Gly Ala Gly Ala Gly Ser Gly Ala Gly
            420                 425                 430
Ala Gly Ser Gly Ala Gly Ala Gly Ser Gly Ala Gly Ala Gly Ser Gly
            435                 440                 445
Ala Gly Ala Gly Ser Gly Val Gly Val Pro Gly Val Gly Val Pro Gly
        450                 455                 460
```

-continued

```
Val Gly Val Pro Gly Val Gly Val Pro Gly Val Gly Val Pro Gly Val
465                 470                 475                 480

Gly Val Pro Gly Val Gly Val Pro Gly Val Gly Val Pro Gly Ala Gly
                485                 490                 495

Ala Gly Ser Gly Ala Gly Ala Gly Ser Gly Ala Gly Ala Gly Ser Gly
            500                 505                 510

Ala Gly Ala Gly Ser Gly Ala Gly Ala Gly Ser Gly Val Gly Val Pro
        515                 520                 525

Gly Val Gly Val Pro Gly Val Gly Val Pro Gly Val Gly Val Pro Gly
    530                 535                 540

Val Gly Val Pro Gly Val Gly Val Pro Gly Val Gly Val Pro Gly Val
545                 550                 555                 560

Gly Val Pro Gly Ala Gly Ala Gly Ser Gly Ala Gly Ala Gly Ser Gly
                565                 570                 575

Ala Gly Ala Gly Ser Gly Ala Gly Ala Gly Ser Gly Ala Gly Ala Gly
            580                 585                 590

Ser Gly Val Gly Val Pro Gly Val Gly Val Pro Gly Val Gly Val Pro
        595                 600                 605

Gly Val Gly Val Pro Gly Val Gly Val Pro Gly Val Gly Val Pro Gly
    610                 615                 620

Val Gly Val Pro Gly Val Gly Val Pro Gly Ala Gly Ala Gly Ser Gly
625                 630                 635                 640

Ala Gly Ala Gly Ser Gly Ala Gly Ala Gly Ser Gly Ala Gly Ala Gly
                645                 650                 655

Ser Gly Ala Gly Ala Gly Ser Gly Val Gly Val Pro Gly Val Gly Val
            660                 665                 670

Pro Gly Val Gly Val Pro Gly Val Gly Val Pro Gly Val Gly Val Pro
        675                 680                 685

Gly Val Gly Val Pro Gly Val Gly Val Pro Gly Val Gly Val Pro Gly
    690                 695                 700

Ala Gly Ala Gly Ser Gly Ala Gly Ala Gly Ser Gly Ala Gly Ala Gly
705                 710                 715                 720

Ser Gly Ala Gly Ala Gly Ser Gly Ala Gly Ala Gly Ser Gly Val Gly
                725                 730                 735

Val Pro Gly Val Gly Val Pro Gly Val Gly Val Pro Gly Val Gly Val
            740                 745                 750

Pro Gly Val Gly Val Pro Gly Val Gly Val Pro Gly Val Gly Val Pro
        755                 760                 765

Gly Val Gly Val Pro Gly Ala Gly Ala Gly Ser Gly Ala Gly Ala Gly
    770                 775                 780

Ser Gly Ala Gly Ala Gly Ser Gly Ala Gly Ala Gly Ser Gly Ala Gly
785                 790                 795                 800

Ala Gly Ser Gly Val Gly Val Pro Gly Val Gly Val Pro Gly Val Gly
                805                 810                 815

Val Pro Gly Val Gly Val Pro Gly Val Gly Val Pro Gly Val Gly Val
            820                 825                 830

Pro Gly Val Gly Val Pro Gly Val Gly Val Pro Gly Ala Gly Ala Gly
        835                 840                 845

Ser Gly Ala Gly Ala Gly Ser Gly Ala Gly Ala Gly Ser Gly Ala Gly
    850                 855                 860

Ala Gly Ser Gly Ala Gly Ala Gly Ser Gly Val Gly Val Pro Gly Val
865                 870                 875                 880

Gly Val Pro Gly Val Gly Val Pro Gly Val Gly Val Pro Gly Val Gly
```

-continued

```
                885                 890                 895
Val Pro Gly Val Gly Val Pro Gly Val Gly Val Pro Gly Val Gly Val
            900                 905                 910
Pro Gly Ala Gly Ala Gly Ser Gly Ala Gly Ala Gly Ser Gly Ala Gly
            915                 920                 925
Ala Gly Ser Gly Ala Gly Ala Gly Ser Gly Ala Gly Ala Gly Ser Met
    930                 935                 940
Asp Pro Gly Arg Tyr Gln Leu Ser Ala Gly Arg Tyr His Tyr Gln Leu
945                 950                 955                 960
Val Trp Cys Gln Lys
                965
```